(12) United States Patent
Narikawa et al.

(10) Patent No.: US 8,802,025 B2
(45) Date of Patent: Aug. 12, 2014

(54) REAGENT KIT FOR SAMPLE ANALYSIS AND SAMPLE ANALYSIS METHOD

(75) Inventors: Tatsuya Narikawa, Kobe (JP); Tomohiro Tsuji, Kobe (JP); Keiko Moriyama, Kobe (JP); Yuji Itose, Kako-gun (JP); Shinichiro Oguni, Kobe (JP); Ayumu Yoshida, Kobe (JP); Saori Suzuki, Kobe (JP); Toshihiro Mizukami, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 313 days.

(21) Appl. No.: 12/677,250

(22) PCT Filed: Sep. 26, 2008

(86) PCT No.: PCT/JP2008/067507
§ 371 (c)(1),
(2), (4) Date: Mar. 9, 2010

(87) PCT Pub. No.: WO2009/041626
PCT Pub. Date: Apr. 2, 2009

(65) Prior Publication Data
US 2010/0330565 A1    Dec. 30, 2010

(30) Foreign Application Priority Data

Sep. 27, 2007  (JP) ................. 2007-252666
Mar. 24, 2008  (JP) ................. 2008-076606

(51) Int. Cl.
  *B01L 3/00*   (2006.01)
  *C12Q 1/70*   (2006.01)
  *C12Q 1/68*   (2006.01)
  *G01N 33/53*  (2006.01)

(52) U.S. Cl.
  USPC ............. 422/430; 435/5; 435/6.1; 435/7.1; 435/7.2

(58) Field of Classification Search
  USPC .............. 422/430; 435/5, 6.1, 7.1, 7.2
  See application file for complete search history.

(56) References Cited

U.S. PATENT DOCUMENTS

| | | |
|---|---|---|
| 5,308,772 A | 5/1994 | Sakata et al. |
| 5,518,928 A | 5/1996 | Cremins et al. |
| 5,538,893 A | 7/1996 | Sakata et al. |
| 5,555,196 A | 9/1996 | Asano |
| 5,555,198 A | 9/1996 | Asano |
| 5,618,733 A | 4/1997 | Sakata |
| 5,631,165 A * | 5/1997 | Chupp et al. ............. 436/43 |
| 5,677,183 A | 10/1997 | Takarada et al. |
| 6,004,536 A * | 12/1999 | Leung et al. ............. 424/9.6 |
| 6,027,709 A | 2/2000 | Little et al. |
| 8,101,414 B2 * | 1/2012 | Mizukami et al. ............. 436/10 |
| 8,163,471 B2 * | 4/2012 | Mizukami et al. ............. 435/4 |
| 2002/0006631 A1 | 1/2002 | Howen et al. |
| 2003/0219850 A1 | 11/2003 | Tsuji et al. |
| 2004/0241770 A1 | 12/2004 | Houwen et al. |
| 2006/0073601 A1 | 4/2006 | Kawashima et al. |

FOREIGN PATENT DOCUMENTS

| | | |
|---|---|---|
| EP | 0 882 983 A2 | 12/1998 |
| EP | 1 865 318 A1 | 12/2007 |
| EP | 1 890 143 A1 | 2/2008 |
| JP | 61-88896 A | 5/1986 |
| JP | 05-149863 A | 6/1993 |
| JP | 06-222059 A | 8/1994 |
| JP | 07-294518 A | 11/1995 |
| JP | 10-339729 A | 12/1998 |
| JP | 2002-148261 A | 5/2002 |
| JP | 2006-105625 A | 4/2006 |

* cited by examiner

*Primary Examiner* — Jezia Riley
(74) *Attorney, Agent, or Firm* — Sughrue Mion, PLLC

(57) ABSTRACT

The present invention provides a reagent kit for analyzing a sample comprising a first reagent containing a cationic surfactant, a nonionic surfactant and an aromatic carboxylic acid and a second reagent containing a fluorescent dye capable of staining nucleic acid, and a method for analyzing a sample using the kit.

8 Claims, 25 Drawing Sheets

| | BASO sample 1 (8 hours after blood collection) | BASO sample 2 (8 hours after blood collection) |
|---|---|---|
| First reagent A<br>Second reagent |  |  |
| First reagent B<br>Second reagent |  |  |
| First reagent C<br>Second reagent |  |  |
| First reagent D<br>Second reagent |  |  |
| First reagent E<br>Second reagent |  |  |
| First reagent F<br>Second reagent |  |  |

| | NRBC sample 1 (8 hours after blood collection) | NRBC sample 2 (8 hours after blood collection) |
|---|---|---|
| First reagent A<br>Second reagent |  |  |
| First reagent B<br>Second reagent |  |  |
| First reagent C<br>Second reagent |  |  |
| First reagent D<br>Second reagent |  |  |
| First reagent E<br>Second reagent |  |  |
| First reagent F<br>Second reagent |  |  |

(A) Correlation of number of total leukocytes y = 0.945x + 357
r = 0.995

(N = 12)

(B) Correlation of ratio of basophils y = 0.815x + 0.122
R = 0.912

(N = 12)

REAGENT KIT FOR SAMPLE ANALYSIS AND SAMPLE ANALYSIS METHOD

CROSS REFERENCE TO RELATED APPLICATIONS

This application is a National Stage of International Application No. PCT/JP2008/067507 filed Sep. 26, 2008, claiming priority based on Japanese Patent Application Nos. 2007-252666 and 2008-076606, filed Sep. 27, 2007 and Mar. 24, 2008 respectively, the contents of all of which are incorporated herein by reference in their entirety.

TECHNICAL FIELD

The present invention relates to a reagent kit and method for analysis of blood cells in a biological sample.

BACKGROUND ART

In the field of laboratory tests, the analysis of blood components in samples is very important when various diseases of circulatory organs or the like of subjects are diagnosed. Depending to the type of diseases, the number of particular blood cells may increase or decrease, or the blood cells which normally do not exist therein appear in the peripheral blood, in some cases.

Recently, various automatic blood cell counters are commercialized in which the principles of flow cytometry are applied. By using such automatic blood cell counters, blood cells in samples can be automatically classified and counted.

Normally, leukocytes can be classified into five species, lymphocytes, monocytes, neutrophils, eosinophils and basophils. Among them, the number of basophils contained in blood samples is small. Therefore, the accuracy of the classification can be improved by measuring basophils in blood samples with the treatment exclusive for basophil measurements, compared to the measurement of basophils with the method in which leukocytes are classified into five species and basophils are measured in one measurement. Basophils have the specific characteristic such that they are less damaged compared to other types of leukocytes under an acidic condition. By utilizing such characteristics, discrimination of basophils from other types of leukocytes with the treatment exclusive for basophils is disclosed in Japanese Unexamined Patent Publication No. SHO 61 (1986)-88896 (Patent Document 1) and Japanese Unexamined Patent Publication No. HEI 7 (1995)-294518 (Patent Document 2).

An emergence of nucleated erythrocytes sometimes causes problems in a measurement of leukocytes. Nucleated erythrocytes have nuclei. In a measurement of leukocytes, even when erythrocytes are treated to be lysed, nuclei of nucleated erythrocytes remain to cause the signal similar to leukocytes, giving false positive error on the measurement of the number of leukocytes. In order to eliminate this effect and obtain the precise number of leukocytes, a blood sample is treated by the treatment exclusive for nucleated erythrocytes to measure the number of nucleated erythrocytes, the number of leukocytes in the same blood sample is measured by a different method, and then the number of nucleated erythrocytes is subtracted from the number of leukocytes obtained. Japanese Unexamined Patent Publication No. HEI 10 (1998)-339729 (Patent Document 3) discloses the discrimination of nucleated erythrocytes from leukocytes by applying the treatment exclusive for nucleated erythrocytes to blood samples.

However, the necessity of the treatments exclusive for respective blood cells as disclosed in the above Patent Documents 1 to 3 for the classification of basophils or nucleated erythrocytes requires a great deal of time and further makes measurement apparatus complicated or upsized. In addition, the usage of multiple reagents exclusive for respective blood cells comes expensive as overall cost for blood test. Accordingly, it is preferable that the treatments exclusive for blood cells are as less as possible.

Both basophils and nucleated erythrocytes can be measured by treating blood samples under an acidic condition. Therefore, there is a possibility that both basophils and nucleated erythrocytes can be measured in one measurement when a blood sample is treated under an acidic condition. Japanese Unexamined Patent Publication No. 2002-148261 (Patent Document 4) discloses that basophils and erythroblasts (nucleated erythrocytes) can be measured by mixing a sample with an aqueous solution containing a surfactant and an erythrocyte lysing agent which allows leukocytes and abnormal cells to be in the state suitable for staining, adding a staining agent containing a fluorescent dye to stain the cells and measuring the fluorescent intensity and the scattered light intensity with a flow cytometer.

DISCLOSURE OF THE INVENTION

Problems that the Invention is to Solve

However, by using the method disclosed in Patent Document 4, basophils are not well separated from leukocytes other than basophils, especially in a blood sample for which a lapse of time has passed after its collection, in some cases.

Thus, the objective of the present invention is to provide a reagent kit and method for measuring a sample which allow clearer discrimination and counting of nucleated erythrocytes and basophils from other types of leukocytes in the sample.

Means for Solving the Problems

The present invention is a reagent kit for analyzing a sample to measure basophils and/or nucleated erythrocytes in the sample comprising:
a first reagent containing a cationic surfactant, a nonionic surfactant and an aromatic carboxylic acid, which can lyse erythrocytes and damage a cell membrane of leukocytes so that a fluorescent dye can permeate therethrough, and
a second reagent containing the fluorescent dye capable of staining nucleic acid.

Further, the present invention is a method for analyzing a sample comprising the following steps:
lysing erythrocytes in the sample and damaging a cell membrane of blood cells so that a fluorescent dye can permeate therethrough, by virtue of the above first reagent, and staining the damaged cells by virtue of the above second reagent,
applying light to the stained cells to obtain scattered light information and fluorescent information, and
classifying and counting basophils and/or nucleated erythrocytes in the sample based on the scattered light information and the fluorescent information.

Effect of the Invention

According to the present invention, nucleated erythrocytes and basophils can be more clearly discriminated from other blood cells and can be counted even in the blood sample for which a lapse of time has passed after its collection, allowing more precise tests and diagnoses of diseases. Although the present invention makes it possible to count nucleated erythrocytes and basophils in one measurement, it may be in some cases sufficient if either one of nucleated erythrocytes and basophils are measured, depending on the purpose of the test. In such case, the present invention also allows such measurements.

BEST MODE FOR CARRYING OUT THE INVENTION

Figure 1:
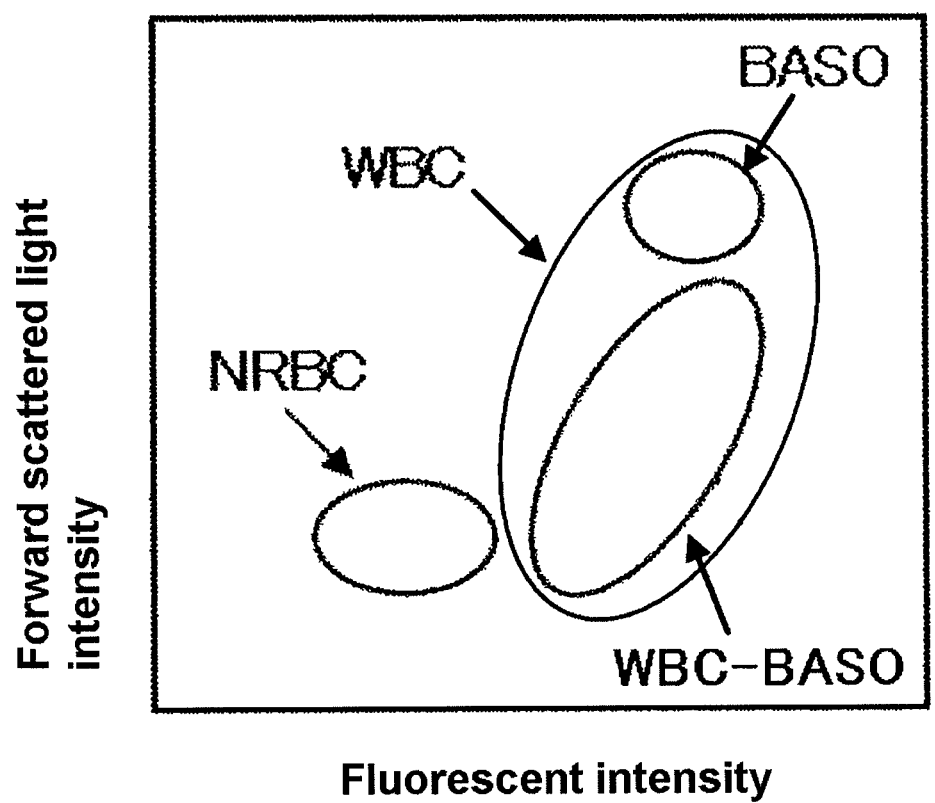
FIG. 1 represents a schematic form of a scattergram when a sample is analyzed using the sample analysis reagent of the present invention.

Basophils are one species of leukocytes and have large acidic granules which are stained with basic dyes. Nucleated erythrocytes are also called as erythroblasts normally and include proerythroblasts, basophilic erythroblasts, polychromatophilic erythroblasts and orthochromatophilic erythroblasts.

As used herein, a "sample" refers to a body fluid sample taken from mammals, preferably human, including blood, bone barrow fluid, urea, a sample taken in apheresis and the like.

The present inventors, as a result of extensive study, have found that nucleated erythrocytes and basophils can be more clearly discriminated from other types of leukocytes by using the first reagent containing a cationic surfactant, a nonionic surfactant and an aromatic carboxylic acid and the second reagent containing a fluorescent dye capable of staining nucleic acid.

According to one embodiment of the present invention, the reagent kit for sample analysis is the reagent kit comprising the first reagent containing a cationic surfactant, a nonionic surfactant and an aromatic carboxylic acid and the second reagent containing a fluorescent dye capable of staining nucleic acid. By treating the sample with the first reagent containing the cationic surfactant, the nonionic surfactant and the aromatic carboxylic acid, erythrocytes in the sample can be lysed and cell membranes of leukocytes and nucleated erythrocytes can be damaged in such extent that the fluorescent dye can permeate the membranes. Due to this, leukocytes other than basophils and nucleated erythrocytes are damaged in the cell membranes and shrink or generate stripped nuclei, while basophils are less damaged in the cell membranes than leukocytes other than basophils and nucleated erythrocytes. Therefore, it is considered that basophils shrink less compared to the leukocytes other than basophils and nucleated erythrocytes. Accordingly, basophils can be discriminated from leukocytes other than basophils and nucleated erythrocytes based on the differences in cell size or shape. Further, by treating the sample with the second reagent containing the fluorescent dye capable of staining nucleic acid, nucleated erythrocytes can be discriminated from leukocytes other than basophils and basophils based on the difference in staining properly with the fluorescent dye.

The cationic surfactant can lyse erythrocytes and damage cell membranes of leukocytes and nucleated erythrocytes. The cationic surfactant is preferably a type of a quaternary ammonium salt or pyridinium salt. The cationic surfactant of the quaternary ammonium salt type is preferably a quaternary ammonium salt having the following general formula (III):

In the above formula (III), $R^{13}$, $R^{14}$ and $R^{15}$ may be the same or different, and are a hydrogen atom, a $C_{1-8}$ alkyl group or a $C_{6-8}$ aralkyl group. $R^{16}$ is a $C_{8-18}$ alkyl group, a $C_{8-18}$ alkenyl group or a $C_{6-18}$ aralkyl group. $X^-$ is an anion.

The $C_{1-8}$ alkyl group for $R^{13}$, $R^{14}$ and $R^{15}$ includes methyl, ethyl, propyl, butyl, pentyl, hexyl, heptyl, octyl and the like. The $C_{6-8}$ aralkyl group for $R^{13}$, $R^{14}$ and $R^{15}$ includes benzyl, phenethyl and the like. Preferably, $R^{13}$, $R^{14}$ and $R^{15}$ are a $C_{1-8}$ alkyl group such as methyl, ethyl and the like.

The $C_{8-18}$ alkyl group for $R^{16}$ includes octyl, decyl, dodecyl, tetradecyl and the like. The $C_{8-18}$ alkenyl group for $R^{16}$ includes octenyl, decenyl, oleyl and the like. The $C_{6-18}$ aralkyl group for $R^{16}$ includes benzyl, phenethyl and the like. Preferably, $R^{16}$ is a $C_{10-18}$ straight chain alkyl group such as decyl, dodecyl, tetradecyl and the like.

The anion $X^-$ includes halogen ions such as $F^-$, $Cl^-$, $Br^-$ and $I^-$, $CF_3SO_3^-$, $BF_4^-$, $ClO_4^-$ and the like.

The cationic surfactant of the pyridinium salt type is preferably the pyridinium salt having the following formula (IV):

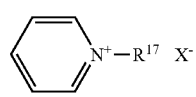
(IV)

In the above formula (IV), $R^{17}$ is a $C_{8-18}$ alkyl group. $X^-$ is an anion.

The $C_{8-18}$ alkyl group includes a $C_{10-18}$ straight chain alkyl group such as decyl, dodecyl, tetradecyl and the like. The anion $X^-$ includes halogen ions such as $F^-$, $Cl^-$, $Br^-$ and $I^-$, $CF_3SO_3^-$, $BF_4^-$, $ClO_4^-$ and the like.

Specific examples of the cationic surfactant includes decyltrimethylammonium bromide, dodecyltrimethylammonium chloride, octyltrimethylammonium bromide, octyltrimethylammonium chloride, lauryltrimethylammonium bromide, lauryltrimethylammonium chloride, myristyltrimethylammonium bromide, myristyltrimethylammonium chloride, laurylpyridinium chloride and the like.

The cationic surfactant is used in the concentration which is sufficient to lyse erythrocytes and damage cell membranes of leukocytes and nucleated erythrocytes. Such preferable concentration can be easily determined by, for example, observing the state of cell membranes or the like under a conventional optical microscope. Specifically, the concentration of the cationic surfactant is preferably 300 to 9000 mg/L, more preferably 400 to 8000 mg/L, and most preferably 500 to 7000 mg/L. However, the concentration can be appropriately adjusted according to the type of the cationic surfactant used.

When the concentration of the cationic surfactant is too low, the accurate discrimination between basophils and leukocytes other than basophils may not be possible in some cases. The reason for this is considered to be that leukocytes are not sufficiently damaged when the concentration of the cationic surfactant is too low, so that the difference in size or shape between basophils and leukocytes other than basophils is small. On the other hand, when the concentration of the cationic surfactant is too high, the accurate discrimination between nucleated erythrocytes and leukocytes other than basophils may not be possible in some cases. The reason for this is considered to be that cell membranes of, particularly, nucleated erythrocytes and leukocytes other than basophils are excessively damaged when the concentration of the cationic surfactant is too high, so that the accurate discrimination between nucleated erythrocytes and leukocytes other than basophils is not possible. Accordingly, when the concentration is within the above range, erythrocytes can be efficiently lysed without excessively damaging cell membranes of leukocytes and nucleated erythrocytes. The power of hemolysis of the cationic surfactant depends on the length of the principal chain. The cationic surfactants having a long principal chain has stronger power for hemolysis, thus providing sufficient effect with smaller amount compared to the ones having a short chain.

In the blood sample for which a lapse of time has passed after its collection, blood cells such as leukocytes are liable to be damaged due to their morphological change. When the cationic surfactant is used for such sample, cell membranes of, particularly, nucleated erythrocytes and leukocytes other than basophils are excessively damaged, so that the accurate discrimination between nucleated erythrocytes and leukocytes other than basophils is not possible in some cases. In such cases, the use of the nonionic surfactant together with the cationic surfactant allows more accurate discrimination between nucleated erythrocytes and leukocytes other than basophils by suppressing the excessive damage on leukocytes and the like. The nonionic surfactant is preferably a polyoxyethylene alkyl ether, a polyoxyethylene polyoxypropylene alkyl ether, a polyoxyethylene castor oil, a polyoxyethylene hydrogenated castor oil, a polyoxyethylene sterol or a polyoxyethylene hydrogenated sterol.

The polyoxyethylene alkyl ether-type nonionic surfactant is preferably the one having the following formula (V):

(V)

In the above formula, $R^{18}$ is a $C_{12-22}$ alkyl group or a $C_{12-22}$ alkenyl group. n is 10 to 30.

The polyoxyethylene polyoxypropylene alky ether-type nonionic surfactant is preferably the one having the following formula (VI):

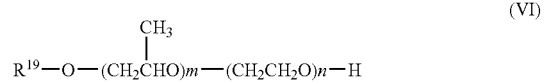
(VI)

In the above formula, $R^{19}$ is a $C_{10-30}$ alkyl group or a C. alkenyl group. m is 1 to 10. n is 10 to 30.

The polyoxyethylene castor oil-type nonionic surfactant is preferably the one having the following formula (VII):

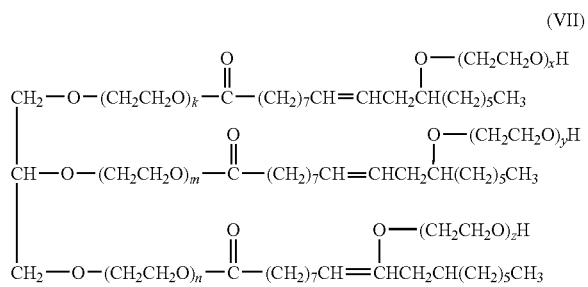
(VII)

In the above formula, the sum of k, n, m, x, y and z is 10 to 60.

The polyoxyethylene hydrogenated castor oil-type nonionic surfactant is preferably the one having the following formula (VIII):

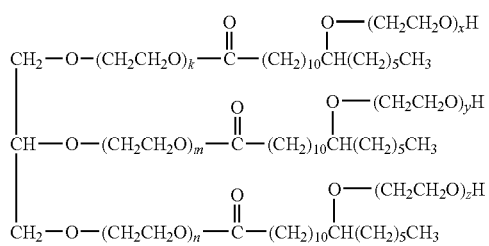

In the above formula, the sum of k, n, m, x, y and z is 10 to 60.

The polyoxyethylene sterol-type nonionic surfactant is preferably the one having the following formula (IX):

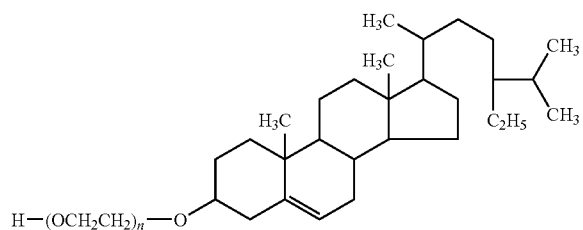

In the above formula, n is 10 to 30.

The polyoxyethylene hydrogenated sterol-type nonionic surfactant is preferably the one having the following formula (X) or (XI):

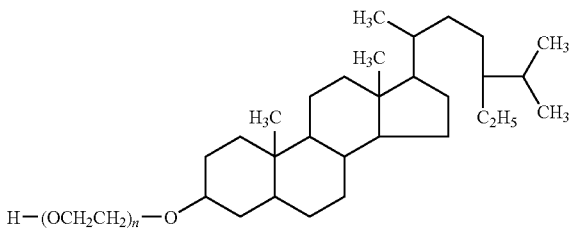

wherein n is 20 to 30;

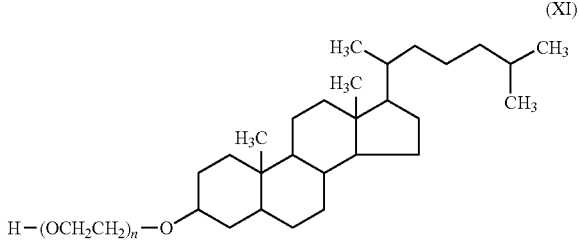

wherein n is 20 to 30.

The $C_{12-22}$ alkyl group includes dodecyl, hexadecyl and the like groups. The $C_{12-22}$ alkenyl group includes oleyl and the like groups. When n in the above formulae (V), (VI) and (IX) to (XI) is too low, membranes of blood cells are excessively damaged; and when n is too high, membranes of blood cells are not damaged sufficiently. Similarly, when the sum of k, n, m, x, y and z in the above formulae (VII) and (VIII) is too low, membranes of blood cells are excessively damaged; and when it is too high, membranes of blood cells are not damaged sufficiently.

The nonionic surfactant specifically includes polyoxyethylene(16) oleyl ether, polyoxyethylene(20) cetyl ether, polyoxyethylene(20) polyoxypropylene(8) cetyl ether, polyoxyethylene(30) polyoxypropylene(6) decyltetradecyl ether, polyoxyethylene(20) castor oil, polyoxyethylene(20) hydrogenated castor oil, polyoxyethylene(50) hydrogenated castor oil, polyoxyethylene(25) phytostanol and the like. Among these, particularly preferred are polyoxyethylene(16) oleyl ether and polyoxyethylene(20) polyoxypropylene(8) cetyl ether.

The concentration of the nonionic surfactant is preferably 500 to 7000 mg/L, more preferably 800 to 6000 mg/L, and most preferably 1000 to 5000 mg/L. However, the concentration can be appropriately adjusted according to the type of the nonionic surfactant used.

When the concentration of the nonionic surfactant is too low, the accurate discrimination between, particularly, nucleated erythrocytes and leukocytes other than basophils may not be possible in some cases, because the excessive damage to cell membranes of leukocytes and nucleated erythrocytes by the cationic surfactant can not be suppressed. On the other hand, when the concentration of the nonionic surfactant is too high, the accurate discrimination between, particularly, basophils and leukocytes other than basophils may not be possible in some cases, because the damage by the cationic surfactant on cell membranes of leukocytes and nucleated erythrocytes is suppressed. Accordingly, when the concentration is within the above range, nucleated erythrocytes and leukocytes other than basophils can be accurately discriminated even when the blood sample for which a lapse of time has passed after its collection.

The first reagent preferably comprises at least one carboxylic acid having at least one aromatic ring in the molecule (herein after referred to as "aromatic carboxylic acid") or a salt thereof. By using the aromatic carboxylic acid, erythrocytes can effectively be lysed in a short time.

When the first reagent without the aromatic carboxylic acid is used in measurements, basophils are detected in a falsely high amount depending on blood samples, in some cases. The reason for this falsely high value is not known, however, it can be hypothesized that blood cells other than basophils or other components in the blood samples present similar size, shape or fluorescent intensity as basophils. By testing the blood samples with the first reagent containing the aromatic carboxylic acid, such phenomena of falsely high value can be prevented.

The aromatic carboxylic acid used is arbitrarily selected from organic acids having at least one aromatic ring in the molecule or salts thereof. Preferred aromatic carboxylic acid includes salicylic acid, phthalic acid, benzoic acid, hydroxybenzoic acid, aminobenzoic acid and salts thereof.

The concentration of the aromatic carboxylic acid or a salt thereof in the first reagent is not specifically limited so long as pH of the first reagent is within the range described below, and is preferably 0.1 to 100 mM and more preferably 0.5 to 50 mM.

When the concentration of the aromatic carboxylic acid is too low, the accurate discrimination of basophils may not be possible because the above effect is not sufficiently exerted. On the other hand, when the concentration of the aromatic carboxylic acid is too high, the accurate discrimination between nucleated erythrocytes and leukocytes other than basophils may not be possible in some cases. Accordingly, when the concentration is within the above range, nucleated erythrocytes and basophils are accurately discriminated from other blood cells.

When the sample is treated with the first reagent, erythrocytes are preferably lysed, which disturb a measurement of nucleated erythrocytes and basophils. Generally, erythrocytes are punctured in the cell membrane thereof at an osmotic pressure of about 150 mOsm/kg or lower and become optically transparent after leakage of hemoglobin from the interior of erythrocytes (hemolysis). The optically transparent erythrocytes do not substantially disturb the measurement using a flow cytometry. The conditions with low osmotic pressure and low pH are preferable for lysis of erythrocytes. The osmotic pressure satisfying these two requirements is 20 mOsm/kg to 150 mOsm/kg. By adjusting the osmotic pressure of the first reagent in this range, erythrocytes can be efficiently lysed, which disturb a measurement of nucleated erythrocytes and basophils.

Basophils have a characteristic such that they are difficult to be destructed compared to other leukocytes under an acidic condition. Accordingly, pH of the first reagent is preferably 2.0 to 4.5, more preferably 2.0 to 3.5. Within this pH range, granules of basophils are stable. In addition, within this pH range, erythrocytes can be efficiently lysed without excessively affecting leukocyte, nucleated erythrocytes and the like. Due to this, scattered light and fluorescence from erythrocytes without nucleus can be low, so that erythrocytes do not substantially affect a measurement of nucleated erythrocytes and leukocytes.

pH of the first reagent may be adjusted with a buffering agent. Preferred buffering agent is the one having pKa within ±2.0 of the desired pH, and includes, for example, malic acid, tartaric acid, malonic acid, succinic acid, citric acid, diglycolic acid and the like. The concentration of the buffering agent in the first reagent is not specifically limited so long as the above pH range can be maintained.

Further, it is suitable to combine the aromatic carboxylic acid and the buffering agent because the performance for discrimination of nucleated erythrocytes can be improved. The combination of the buffering agent and aromatic carboxylic acid includes, for example, malic acid and salicylic acid or a salt thereof, malic acid and phthalic acid or a salt thereof, citric acid and salicylic acid or a salt thereof, citric acid and phthalic acid or a salt thereof, malic acid and benzoic acid or a salt thereof, malic acid and phthalic acid or a salt thereof and benzoic acid or a salt thereof.

In order to adjust the osmotic pressure of the first reagent in a range suitable for the lysis of erythrocytes, an electrolyte such as NaCl, KCl, or a saccharide can be used. The osmotic pressure can also be adjusted by means of the concentration of the buffering agent.

The first reagent can be obtained by dissolving the surfactants and the aromatic carboxylic acid or a salt thereof as well as the optional buffering agent in an appropriate solvent so that the above concentrations can be obtained, and optionally adjusting pH with NaOH, HCl or the like. The appropriate solvent is not specifically limited so long as it can dissolve the above components, and includes, for example, water, organic solvents, mixtures thereof and the like. The organic solvents include alcohols, ethylene glycol and dimethylsulfoxide (hereinafter referred to as "DMSO").

The second reagent comprises the fluorescent dye capable of staining nucleic acid. When blood cells treated with the first reagent are stained with the fluorescent dye capable of staining nucleic acid, leukocytes are intensely stained and emit intense fluorescence. On the other hand, nucleated erythrocytes are faintly stained and emit faint fluorescence. Due to the difference in the liability to be stained with the fluorescent dye, nucleated erythrocytes can be discriminated from basophils or leukocytes other than basophils. The mechanism for the production of the difference in fluorescent intensity between leukocytes and nucleated erythrocytes is not elucidated, however, it may be because the incorporation of the dye into cell nucleus is inhibited due to the condensation of nucleus (DNA) of nucleated erythrocytes.

The fluorescent dye is not specifically limited so long as it can stain nucleic acid, and includes the ones which are generally used in the art. The fluorescent dye contained in the second reagent includes the fluorescent dyes of the following formulae (I) and (II):

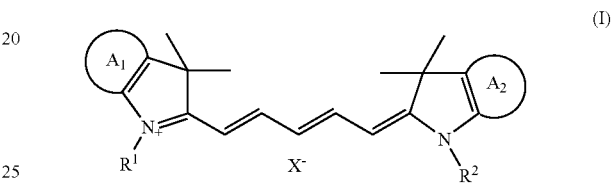

(I)

wherein $R^1$ and $R^2$ are, the same or different from each other, an alkyl group;

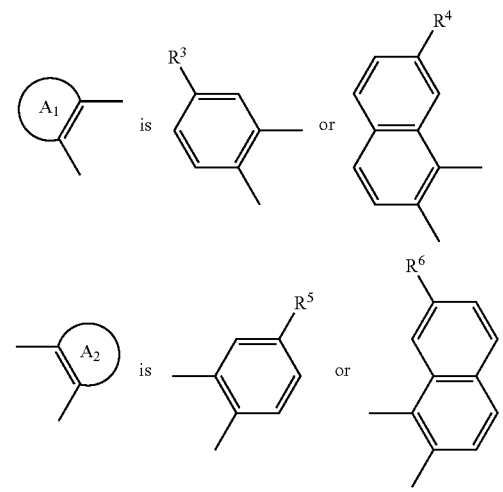

$R^3$, $R^4$, $R^5$ and $R^6$ are, the same or different each other, a hydrogen atom or an alkyl group; and $X^-$ is an anion;

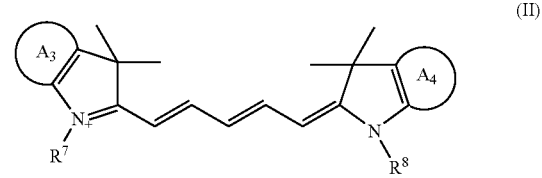

(II)

wherein $R^7$ and $R^8$ are, the same or different from each other, an alkyl group optionally containing an acidic group;

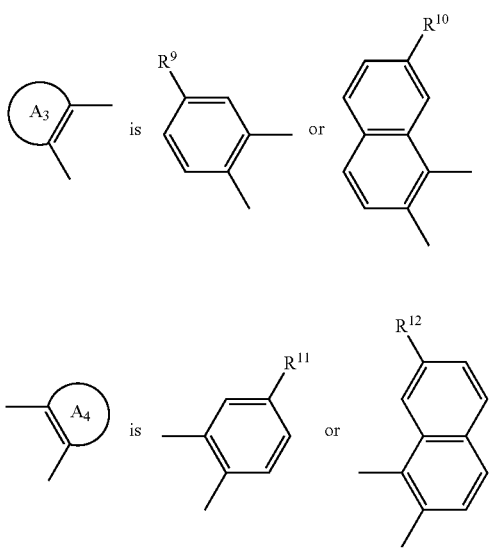

and $R^9$, $R^{10}$, $R^{11}$ and $R^{12}$ are, the same or different from each other, a hydrogen atom or an acidic group, provided that either one of $R^7$ to $R^{12}$ is/has an acidic group; and the acidic group which may present in $R^7$ to $R^{12}$ may form a salt, provided that either one of the acidic group(s) which may present in $R^7$ to $R^{12}$ is a group from which a proton has been liberated.

In the present specification, the alkyl group in the above formulae (I) and (II) may be either of a straight chain or a branched chain. The number of carbon atoms of the alkyl group is generally 1 to 20 and preferably 1 to 10. It is more preferably 1 to 6 in view of the water solubility of the fluorescent dye. Preferred examples of the alkyl group include methyl, ethyl, propyl, butyl, pentyl, hexyl and the like.

$X^-$ in the formula (I) includes halogen ions such as $F^-$, $Cl^-$, $Br^-$ and $I^-$, $CF_3SO_3^-$, $BF_4^-$, $ClO_4^-$ and the like.

As used herein, the acidic group which may be present in the formula (II) includes both a group capable of liberating a proton and a group capable of releasing a proton from which the proton has been liberated. The group capable of liberating a proton includes a carboxyl, sulfonic, phosphoric or the like group, and is preferably a sulfonic group.

The acidic group may form a salt. The salt includes an alkali metal salt such as a sodium, potassium or the like salt. It is preferably a sodium salt.

The fluorescent dye of the formulae (I) and (II) used can be one or more species. The fluorescent dye can be obtained from Hayashibara Biochemical Laboratories, Inc.

The concentration of the dye in the sample analysis reagent of the present invention can be appropriately selected according to the type of the dye, and generally is 0.01 to 100 mg/L, preferably 0.1 to 10 mg/L and more preferably 0.2 to 6.0 mg/L.

The fluorescent dye of the formulae (I) and (II) comprised in the second reagent stains leukocytes intensely because it has higher affinity towards leukocytes than nucleated erythrocytes. Accordingly, based on the difference in the fluorescence emitted from cells stained with the fluorescent dye, nucleated erythrocytes can be more precisely discriminated from leukocytes other than basophils and basophils.

The second reagent can be obtained by dissolving the fluorescent dye in an appropriate solvent so that the above concentration can be obtained. The appropriate solvent is not specifically limited so long as it can dissolve the fluorescent dye, and includes water, organic solvents, the mixture thereof and the like. The organic solvents include alcohols, ethylene glycol, DMSO and the like. Some fluorescent dyes have low long-term stability in aqueous solutions, and in such cases, they are preferably dissolved in the organic solvents.

The reagent kit for sample analysis is preferably mixed with the sample in such amount that the volume ratio of the first reagent:the second reagent:the sample of 10 to 500:1 to 10:1, more preferably 20 to 100:2 to 5:1 is obtained. By employing such ratio for mixing the first reagent, the second reagent and the sample to obtain a measurement sample, erythrocytes are smoothly lysed and blood cell components are satisfactorily stained. The sample amount of a few microliters to 100 μl allows smooth measurements.

The method for sample analysis according to one embodiment of the present invention comprises the steps of:

lysing erythrocytes on the sample and damaging a cell membrane of blood cells so that the fluorescent dye can permeate therethrough, by virtue of the above first reagent, and staining the damaged blood cells by virtue of the above second reagent, applying light to the stained blood cells to obtain scattered light information and fluorescent information, and classifying and counting basophils and/or nucleated erythrocytes in the sample based on the scattered light information and the fluorescent information.

In the staining step, the first reagent, the second reagent and the sample are mixed. In this step, the cationic surfactant, the nonionic surfactant and the aromatic carboxylic acid in the first reagent lyse erythrocytes in the sample and damage cell membranes of the blood cells so that a fluorescent dye can permeate therethrough. Accordingly, by mixing the first reagent, the second reagent and the sample, the target blood cells can effectively stained with the fluorescent dye.

In the staining step, any order may be employed for the mixing of the first reagent, the second reagent and the sample. The first reagent and the second reagent may be mixed, and then this mixture may be mixed with the sample. Alternatively, the first reagent and the sample may be mixed, and then this mixture may be mixed with the second reagent. Similar measurement results can be obtained with any order.

In the staining step, the mixture of the first reagent, the second reagent and the sample is preferably reacted at 15 to 50° C., preferably at 30 to 45° C. for 5 to 120 seconds, preferably 5 to 30 seconds.

The blood cells stained in the staining step can be analyzed with a flow cytometer. The analysis of blood cells using a flow cytometer is now explained. The stained blood cells are applied with light when they are passing through a flow cell of the flow cytometer, thus allowing scattered light information and fluorescent information be obtained. The scattered light information is not specifically limited so long as it is scattered light measurable by conventional commercial flow cytometer, and includes the width of pulse, intensity and the like of scattered light such as forward scattered light (e.g. light-receiving angle of approximately 0 to 20 degrees), side scattered light (e.g. light-receiving angle of approximately 90 degrees). Generally, side scattered light reflects internal information such as nuclei and granules of the cells, and forward scattered light reflects size information of the cells. In the method of the present embodiment, it is preferable that the scattered light information includes forward scattered light intensity and side scattered light intensity.

The fluorescent information is obtained by applying light having an appropriate wave length to the measurement sample and measuring the excited fluorescence. According to the fluorescent dye used, appropriate receiving wave length can be selected. The fluorescence is emitted from nucleic acid and granules in the cells which are stained with the fluorescent dye.

The light source of the flow cytometer used is not specifically limited, and is selected among the light sources which have a suitable wave length for excitation of the fluorescent dye. For example, red semiconductor laser, blue semiconductor laser, argon laser, He—Ne laser may be used. Particularly, the semiconductor lasers are inexpensive compared to gas lasers, and hence are preferable.

Based on thus measured scattered light and fluorescence, nucleated erythrocytes and basophils can be discriminated from other components and counted. This step preferably comprises, for example, (1) obtaining a scattergram having two axes of the fluorescent information and the forward scattered light information, (2) obtaining a scattergram having two axes of the forward scattered light information and the side scattered light information, and (3) analyzing the respective obtained scattergrams with an appropriate analytical software.

Figure 2:
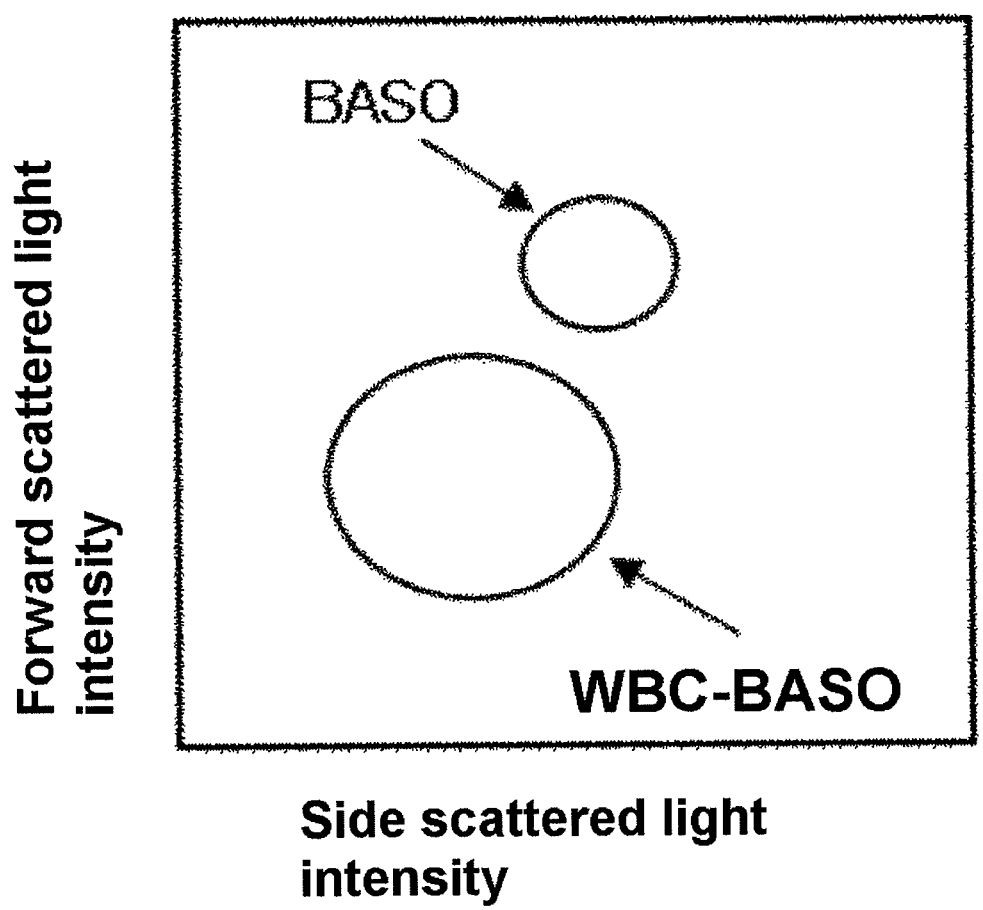
FIG. 2 represents a schematic form of a scattergram when a sample is analyzed using the sample analysis reagent of the present invention.

In the scattergram having the x-axis for the fluorescent intensity and the y-axis for the forward scattered light, as shown in FIG. 1 for example, nucleated erythrocytes, basophils and leukocytes other than basophils are distributed to form clusters respectively. In this figure, NRBC represents the cluster of nucleated erythrocytes, BASO represents the cluster of basophils, WBC-BASO represents the cluster of leukocytes other than basophils and WBC represents the cluster of leukocytes. In such scattergram, nucleated erythrocytes appear in the region whose fluorescent intensity is lower than that of leukocytes. Accordingly, leukocytes can be clearly discriminated from nucleated erythrocytes. Further, basophils appear in the region whose size is bigger, i.e. whose fluorescent intensity is higher than that of leukocytes other than basophils. Accordingly, basophils can be discriminated from leukocytes other than basophils. When blood samples containing high amount of leukocytes or blood samples for which a lapse of time has passed after their collection are measured, basophils and leukocytes other than basophils may not be precisely discriminated in the scattergrams employing fluorescent intensity and forward scattered light intensity. In such cases, the forward scattered light information and the side scattered light information can be utilized. In the scattergram having the x-axis for the side scattered light intensity and the y-axis for the forward scattered light intensity, as shown in FIG. 2 for example, basophils and leukocytes other than basophils are distributed to form clusters respectively. In this figure, BASO represents the cluster of basophils and WBC-BASO represents the cluster of leukocytes other than basophils. In such scattergram, basophils appear in the region whose side scattered light intensity and forward scattered intensity are higher than those of other leukocytes. Accordingly, basophils can be discriminated from other leukocytes. Further, as described above, nucleated erythrocytes can be discriminated from other leukocytes according to FIG. 1. Therefore, the cells which are included in both regions in FIGS. 1 and 2 can be calculated as basophils, so that more precise measurement of basophils can be carried out.

The positions of the clusters for each blood cells appearing on scattergrams can be identified by treating samples respectively containing each blood cells with the reagent kit of the present embodiment and carrying out the measurements.

The number and ratio of nucleated erythrocytes and basophils can be calculated by analyzing the clusters on scattergrams with an appropriate analytical software. Specifically, when a cell cluster is identified on a scattergram in a position where certain cells are supposed to appear, the center of this cluster is identified. The border of this cell cluster can be identified as an area which is between the center and an area in which other cell cluster appears and is until a part in which the concerned certain cell cluster appears. The cells appearing in this identified area can be counted as the concerned certain cells. In addition, by counting leukocytes other than basophils, the ratio of basophils to total leukocytes (basophils/total leukocytes; hereinafter referred to as "the ratio of basophils") and the ratio of nucleated erythrocytes to total leukocytes (nucleated erythrocytes/total leukocytes; hereinafter referred to as "the ratio of nucleated erythrocytes") can be calculated. The ratio of nucleated erythrocytes is generally represented as a percentage of the appeared nucleated erythrocytes per 100 leukocytes, and explained with the unit "cells/100 WBCs".

By using the reagent kit and method for sample analysis according to the present embodiments, the clusters formed by nucleated erythrocytes and basophils, respectively, are clearly separated from the clusters formed by other blood cells, so that more precise counting can be carried out.

The present invention is further explained by the following Examples. However, it should be recognized that various alterations and modifications can be effected on the present invention and the scope thereof is not limited to the following Examples.

EXAMPLES

The cationic surfactants used in the following Examples are decyltrimethylammonium bromide (DTAB) and dodecyltrimethylammonium chloride (LTAC).

The nonionic surfactants used in the following Examples are as follows:

Polyoxyethylene(16) oleyl ether (product name: NIKKOL BO-16);

Polyoxyethylene(20) cetyl ether (product name: NIKKOL BC-20TX);

Polyoxyethylene(20) polyoxypropylene(8) cetyl ether (product name: NIKKOL PBC-44);

Polyoxyethylene(30) polyoxypropylene(6) decyltetradecyl ether (product name: NIKKOL PEN-4630);

Polyoxyethylene(20) castor oil (product name: NIKKOL CO-20TX);

Polyoxyethylene(20) hydrogenated castor oil (product name: NIKKOL HCO-20);

Polyoxyethylene(50) hydrogenated castor oil (product name: NIKKOL HCO-50);

Polyoxyethylene(25) phytostanol (product name: NIKKOL BPSH-25).

All of the above can be obtained from Nikko Chemicals Co., Ltd.

The aromatic carboxylic acids used in the following Examples are salicylic acid, phthalic acid, benzoic acid, hydroxybenzoic acid and aminobenzoic acid.

The fluorescent dyes used in the following Examples are NK-529, NK-2670, NK-3750, NK-3383, NK-1840, NK-9001, NK-9003, NK-2929, NK-3375, NK-5056, NK-3266 and NK-3620. All of these can be obtained from Hayashibara Biochemical Laboratories, Inc. The chemical formulae of these dyes are presented in Table 1.

TABLE 1

| General formulae | Name of dye | Structure R1 | R2 | R3 | R4 | X |
|---|---|---|---|---|---|---|
| (structure 1) | NK-529 | $CH_3$ | $CH_3$ | H | H | $I^-$ |
| | NK-2670 | $CH_3$ | $CH_3$ | H | H | $ClO_4^-$ |
| | NK-3750 | $CH_3$ | $CH_3$ | H | H | $BF_4^-$ |
| | NK-3383 | $C_4H_9$ | $C_4H_9$ | H | H | $ClO_4^-$ |
| | NK-1840 | $(CH_2)_3SO_3^-$ | $(CH_2)_3SO_3Na$ | H | H | — |
| | NK-9001 | $(CH_2)_4SO_3^-$ | $(CH_2)_4SO_3Na$ | H | H | — |
| | NK-9003 | $C_4H_9$ | $C_4H_9$ | $SO_3Na$ | $SO_3^-$ | — |
| (structure 2) | NK-2929 | $CH_3$ | $CH_3$ | H | H | $ClO_4^-$ |
| | NK-3375 | $CH_3$ | $CH_3$ | H | H | $I^-$ |
| | NK-5056 | $(CH_2)_4SO_3^-$ | $(CH_2)_4SO_3 \cdot N(H)(C_2H_5)_3$ | H | H | — |
| (structure 3) | NK-3266 | $CH_3$ | $CH_3$ | H | H | $ClO_4^-$ |
| | NK-3620 | $C_4H_9$ | $C_4H_9$ | H | H | $ClO_4^-$ |

Comparative Example 1

In this Comparative Example, the blood samples for which about 8 hours have passed after their collection were analyzed by using the conventional method.

The blood samples respectively taken from three subjects were measured in the automatic blood cell counter XE-2100 (Sysmex Corporation: equipped with red semiconductor laser (633 nm)) to count the number of total leukocytes and the number of basophils. Based on these counting results, the ratio of basophils was calculated. Stromatolyser-FBII (Sysmex Corporation) was used as the reagent. The blood samples for which about 8 hours have passed after their collection were measured.

As results, it was confirmed that the basophil contents in these samples were above the normal value (hereinafter these samples are referred to as BASO samples 1, 2 and 3, respectively). The ratio of basophils in the BASO samples 1, 2 and 3 were 0.8%, 3.4% and 1.6%, respectively. These results were used as references for Examples 1 and 2.

Nucleated erythrocytes contained in the blood samples taken from three subjects different from the above-described subjects were measured with the automatic blood cell counter XE-2100 to count the number of total leukocytes and number of nucleated erythrocytes. Based on the counting results, the ratio of nucleated erythrocytes was calculated. Stromatolyser-NR (Sysmex Corporation) was used as the reagent. The blood samples for which about 8 hours have passed after their collection were measured.

As results, it was confirmed that nucleated erythrocytes were present in these samples (hereinafter these samples are referred to as NRBC samples 1, 2 and 3, respectively). The ratio of nucleated erythrocytes in the NRBC samples 1, 2 and 3 were 4.4 cells/100 WBCs, 1.9 cells/100 WBCs and 1.3 cells/100 WBCs, respectively. These results were used as references for Examples 1 and 2.

Example 1

In this Example, the first and second reagents having the following compositions were prepared and the blood samples for which about 8 hours have passed after their collection were measured with these reagents.

The pH of the first reagent is 3.0.

First Reagent A:
It is the aqueous solution containing 0.5 mM of sodium salicylate, 10 mM of DL-malic acid, 2000 ppm of LTAC, and 1000 ppm of BO-16.

First Reagent B:
It is the aqueous solution containing 0.5 mM of sodium salicylate, 10 mM of DL-malic acid, 1500 ppm of LTAC, and 1000 ppm of PBC-44.

First Reagent C:

It is the aqueous solution containing 10 mM of sodium salicylate, 2000 ppm of LTAC, and 1000 ppm of BO-16.

First Reagent D:

It is the aqueous solution containing 10 mM of sodium salicylate, 1500 ppm of LTAC, and 1000 ppm of PBC-44.

First Reagent E:

It is the aqueous solution containing 0.5 mM of potassium hydrogen phthalate, 10 mM of DL-malic acid, 2000 ppm of LTAC, and 1000 ppm of BO-16.

First Reagent F:

It is the aqueous solution containing 2 mM of potassium hydrogen phthalate, 10 mM of DL-malic acid, 1500 ppm of LTAC, and 1000 ppm of PBC-44.

Second Reagent:

It is the one in which 15 mg of NK-3383 was dissolved in ethylene glycol 100 mL.

The first reagent (1 mL), 20 μL of the second reagent and 20 μl of the blood sample (BASO sample 1, 2 or 3 or NRBC sample 1, 2 or 3) were mixed thoroughly, and thus obtained mixture was allowed to react at 40° C. for 10 seconds to obtain the measurement sample. The measurement sample was introduced to a detecting part of the flow cytometer having an excitation light source with 633 nm, and an excitation light was applied to the cells in the measurement sample. The scattered light signal and fluorescent signal emitted from the cells were detected and analyzed to measure basophils, nucleated erythrocytes and total leukocytes in the measurement sample. This measurement was carried out with the automatic blood cell counter XE-2100.

BASO samples 1 and 2 and NRBC samples 1 and 2 for which about 8 hours have passed after their collection were examined.

Figure 3:
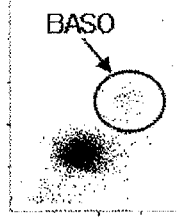
FIG. 3 represents scattergrams when samples are analyzed using the sample analysis reagents in Example 1.
Figure 3:
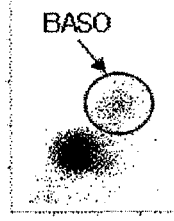
Figure 3:
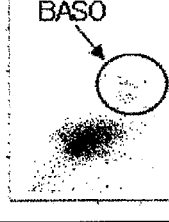
Figure 3:
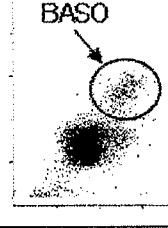
Figure 3:
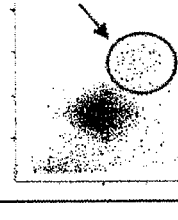
Figure 3:
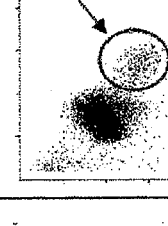
Figure 3:
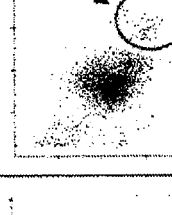
Figure 3:
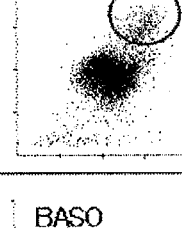
Figure 3:
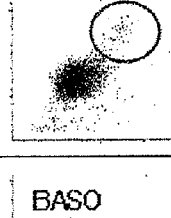
Figure 3:
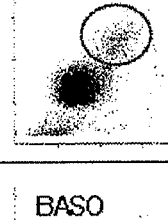
Figure 3:
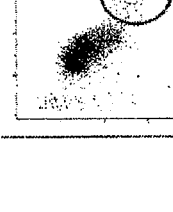
Figure 3:
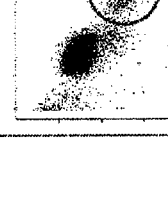
Figure 4:
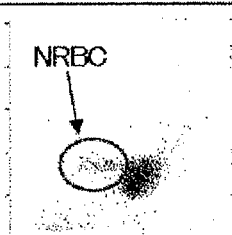
FIG. 4 represents scattergrams when samples are analyzed using the sample analysis reagents in Example 1.
Figure 4:
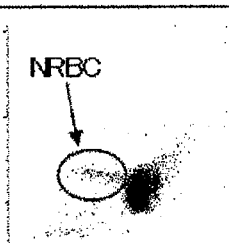
Figure 4:
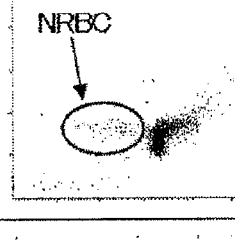
Figure 4:
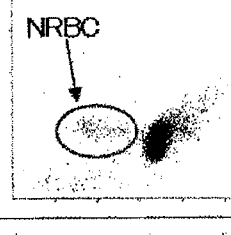
Figure 4:
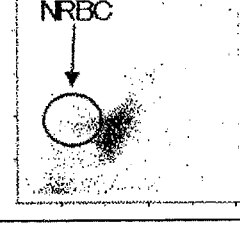
Figure 4:
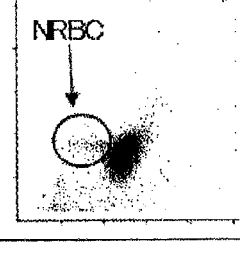
Figure 4:
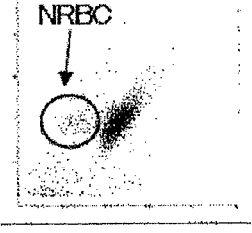
Figure 4:
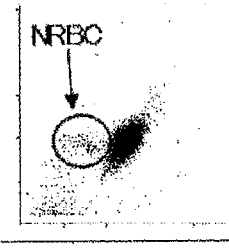
Figure 4:
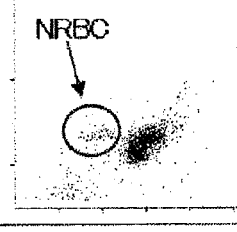
Figure 4:
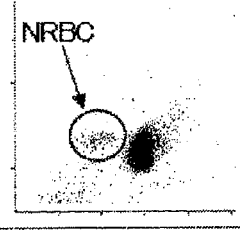
Figure 4:
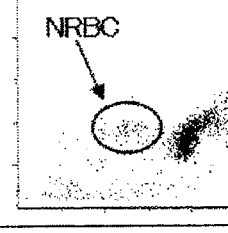
Figure 4:
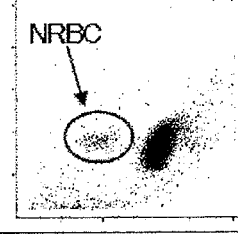

A first scattergram having two axes of the forward scattered light intensity and the fluorescent intensity and a second scattergram having two axes of the forward scattered light intensity and the side scattered light intensity were obtained for the measurement sample. FIG. 3 shows the second scattergrams obtained in the measurements of BASO samples 1 and 2 for which about 8 hours have passed after their collection, and FIG. 4 shows the first scattergrams obtained in the measurements of NRBC samples 1 and 2 for which about 8 hours have passed after their collection.

Based on these scattergrams, total leukocytes, basophils and nucleated erythrocytes were counted and the ratio of basophils and the ratio of nucleated erythrocytes were calculated. Table 2 shows the ratios of basophils of BASO samples 1 and 2 for which 8 hours have passed after their collection, which were calculated in Comparative Example 1 and the present Example. Table 3 shows the ratios of nucleated erythrocytes of NRBC samples 1 and 2 for which 8 hours have passed after their collection, which were calculated in Comparative Example 1 and the present Example.

TABLE 2

| Example | | Ratio of basophils (%) | Ratio of basophils in Comparative Example (%) |
|---|---|---|---|
| Samples used | Reagents used | | |
| BASO sample 1 (8 hours after blood collection) | First reagent A and second reagent | 1.1 | 0.8 |
| | First reagent B and second reagent | 1.1 | |
| | First reagent C and second reagent | 1.2 | |
| | First reagent D and second reagent | 1.1 | |
| | First reagent E and second reagent | 1.2 | |
| | First reagent F and second reagent | 1.2 | |
| BASO sample 2 (8 hours after blood collection) | First reagent A and second reagent | 3.5 | 3.4 |
| | First reagent B and second reagent | 3.8 | |
| | First reagent C and second reagent | 3.5 | |
| | First reagent D and second reagent | 3.6 | |
| | First reagent E and second reagent | 3.7 | |
| | First reagent F and second reagent | 3.7 | |

TABLE 3

| Example | | Ratio of nucleated erythrocytes (cells/100 WBCs) | Ratio of nucleated erythrocytes in Comparative Example (cells/100 WBCs) |
|---|---|---|---|
| Samples used | Reagents used | | |
| NRBC sample 1 (8 hours after blood collection) | First reagent A and second reagent | 5.3 | 4.4 |
| | First reagent B and second reagent | 4.6 | |
| | First reagent C and second reagent | 4.2 | |
| | First reagent D and second reagent | 4.5 | |
| | First reagent E and second reagent | 4 | |
| | First reagent F and second reagent | 4.2 | |
| NRBC sample 2 (8 hours after blood collection) | First reagent A and second reagent | 1.8 | 1.9 |
| | First reagent B and second reagent | 1.8 | |
| | First reagent C and second reagent | 2.1 | |
| | First reagent D and second reagent | 1.8 | |
| | First reagent E and second reagent | 2 | |
| | First reagent F and second reagent | 2 | |

FIG. 3 shows that basophils are clearly discriminated from leukocytes other than basophils when the sample analysis reagents according to the present embodiment were used. FIG. 4 shows that nucleated erythrocytes are clearly discriminated from basophils and leukocytes other than basophils when the sample analysis reagents according to the present embodiment were used. Thus, because basophils and nucleated erythrocytes are clearly discriminated respectively, the number and ratio thereof to total leukocytes were precisely obtained by identifying cells appearing in certain areas on the scattergrams as shown in FIGS. 3 and 4 as basophils and nucleated erythrocytes.

Tables 2 and 3 show that the ratios calculated in Example 1 were closely analogous to the ratios calculated in Comparative Example 1. Therefore, it was confirmed that nucleated erythrocytes and basophils can be measured with the sample analysis reagents of the present Example as precisely as the case when other reagent was used for the measurements.

Example 2

In this Example, the first and second reagents of Example 1 were used to measure the blood samples for which about 50 hours have passed after their collection. The method for measurement was the same as Example 1 except for the used blood samples. BASO sample 2 or 3 and NRBC sample 2 or 3 for which about 50 hours have passed after their collection were measured in this Example.

Among the first reagents A to F in Example 1, the first reagents A, B, E and F were used for the measurements of BASO sample 2 and NRBC sample 2, and the first reagents C and D were used for the measurements of BASO sample 3 and NRBC sample 3.

Figure 5:
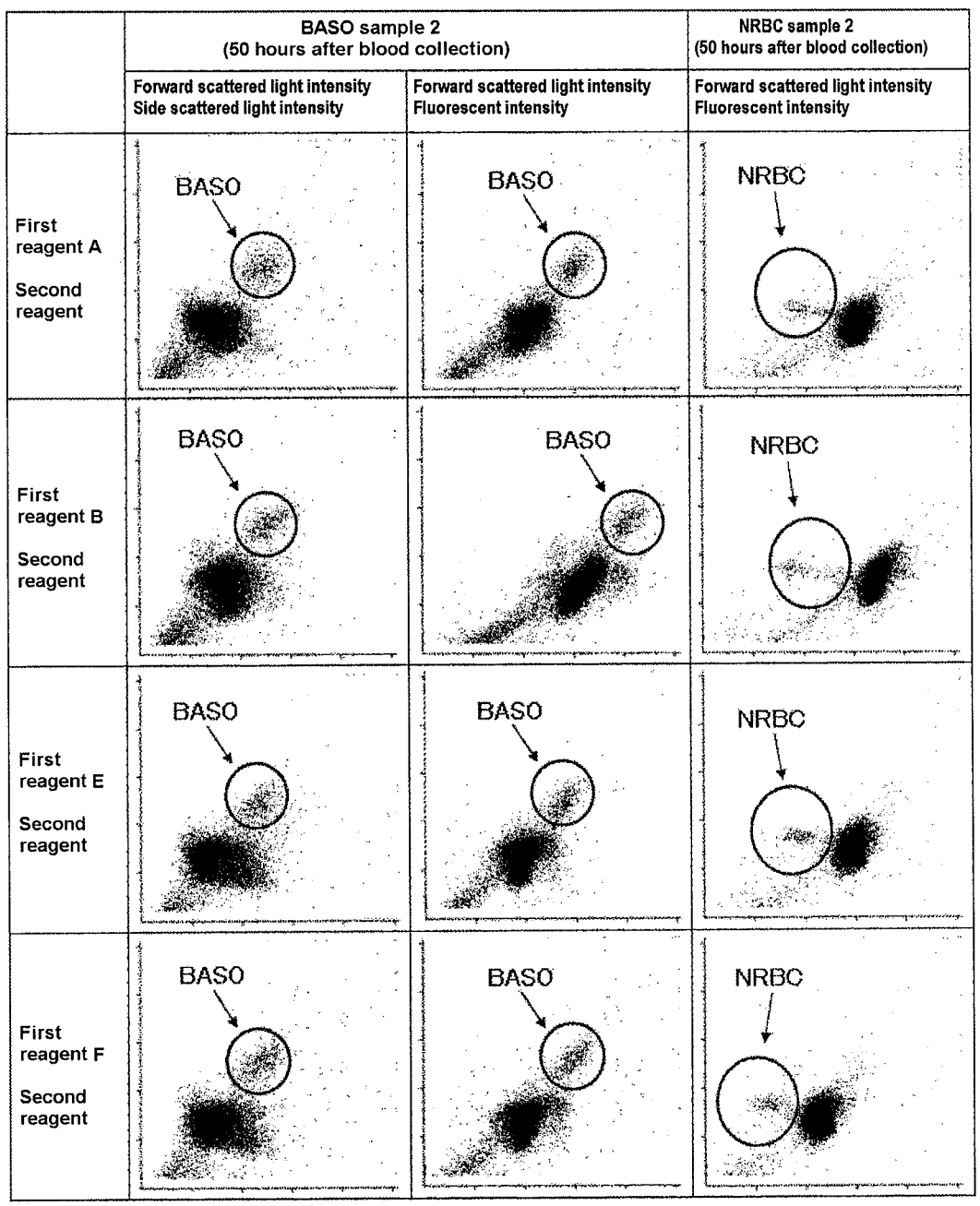
FIG. 5 represents scattergrams when samples are analyzed using the sample analysis reagents in Example 2.
Figure 6:
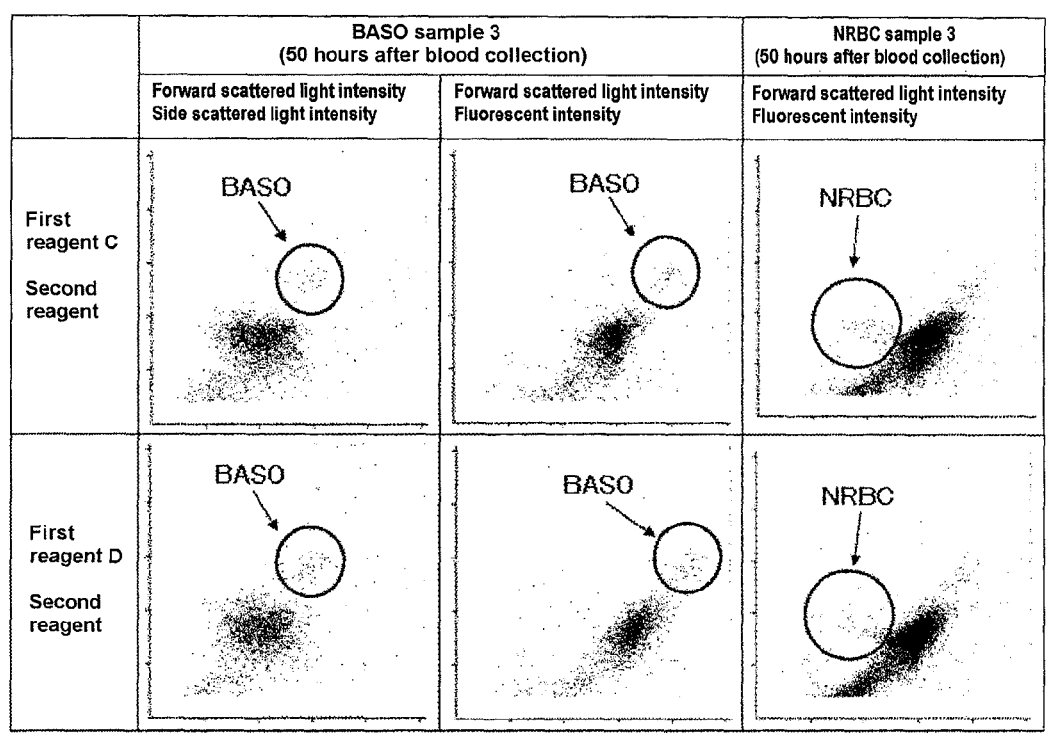
FIG. 6 represents scattergrams when samples are analyzed using the sample analysis reagents in Example 2.
Figure 7:
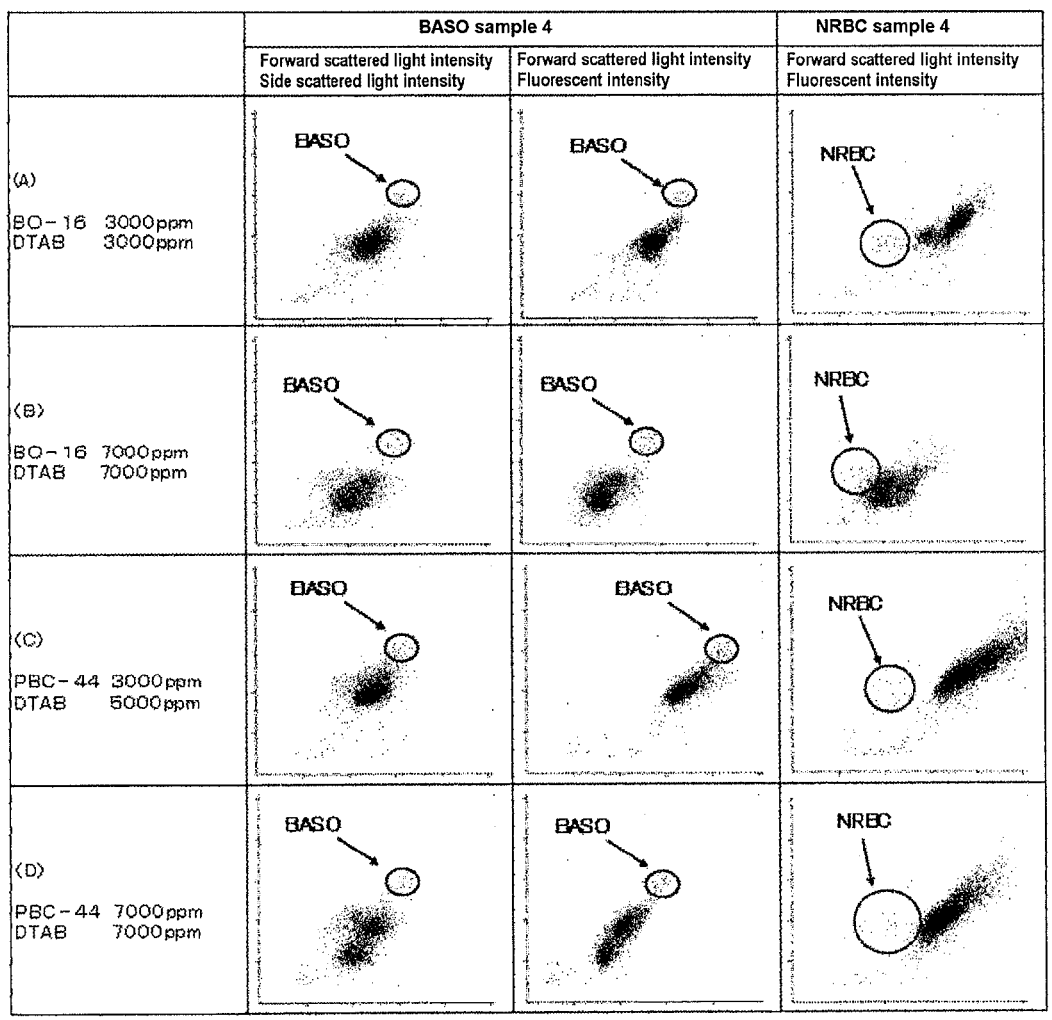
FIG. 7 represents scattergrams when samples are analyzed using the sample analysis reagents in Example 3.
Figure 8:
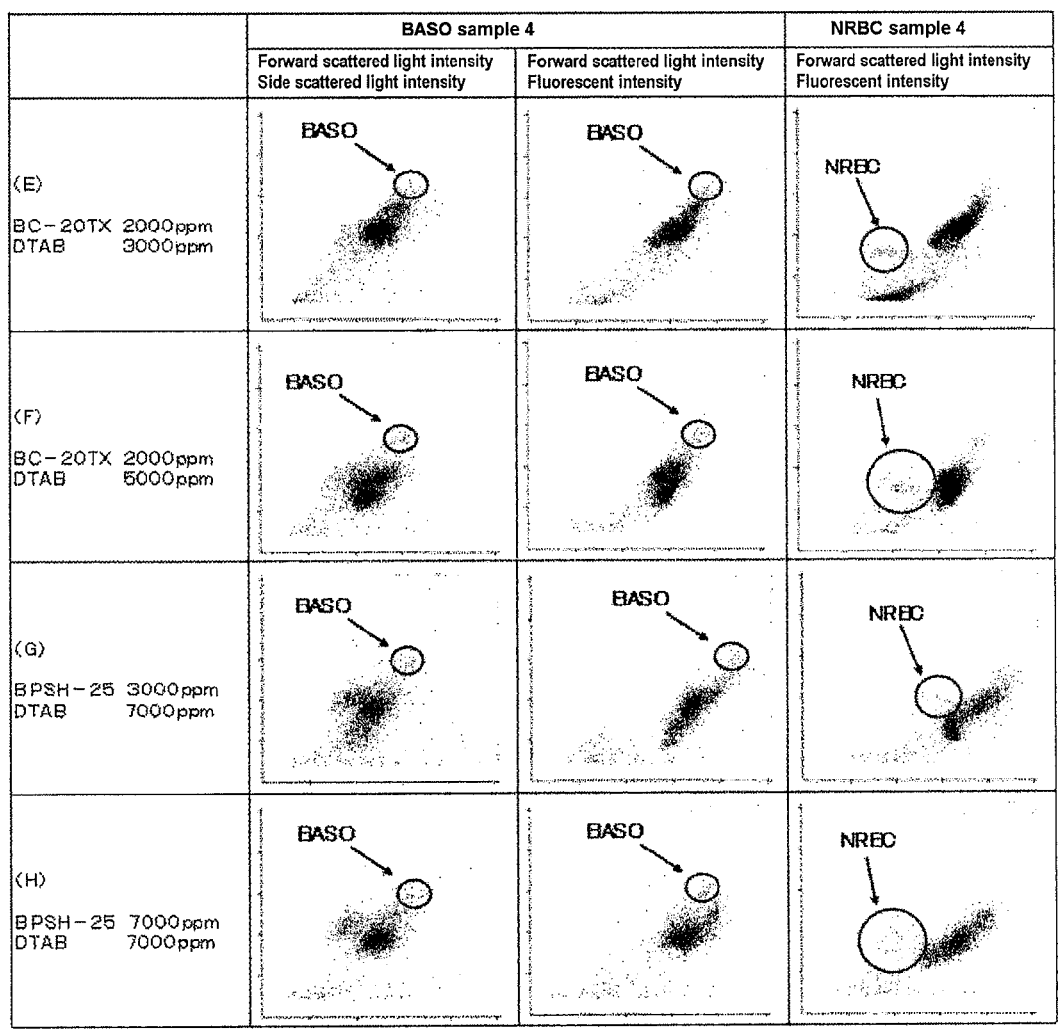
FIG. 8 represents scattergrams when samples are analyzed using the sample analysis reagents in Example 3.
Figure 9:
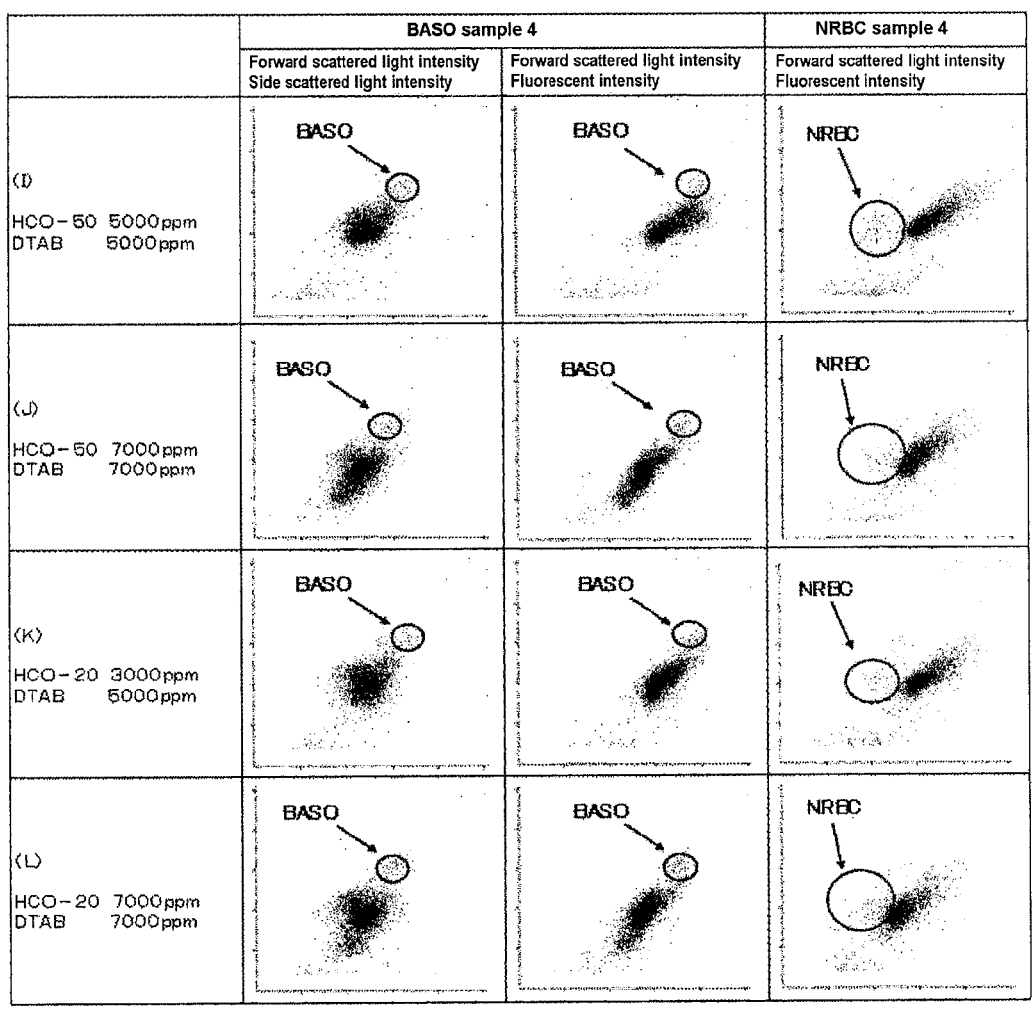
FIG. 9 represents scattergrams when samples are analyzed using the sample analysis reagents in Example 3.
Figure 10:
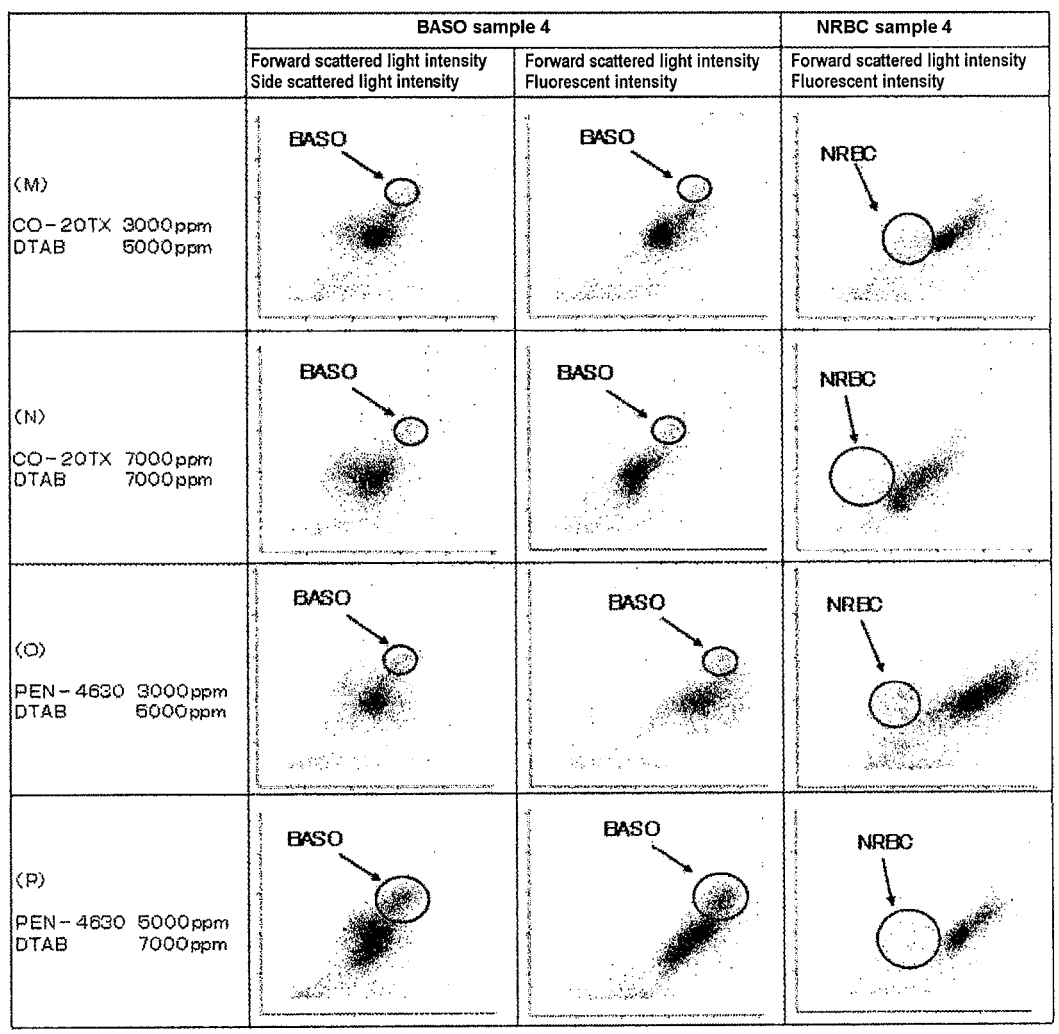
FIG. 10 represents scattergrams when samples are analyzed using the sample analysis reagents in Example 3.
Figure 11:
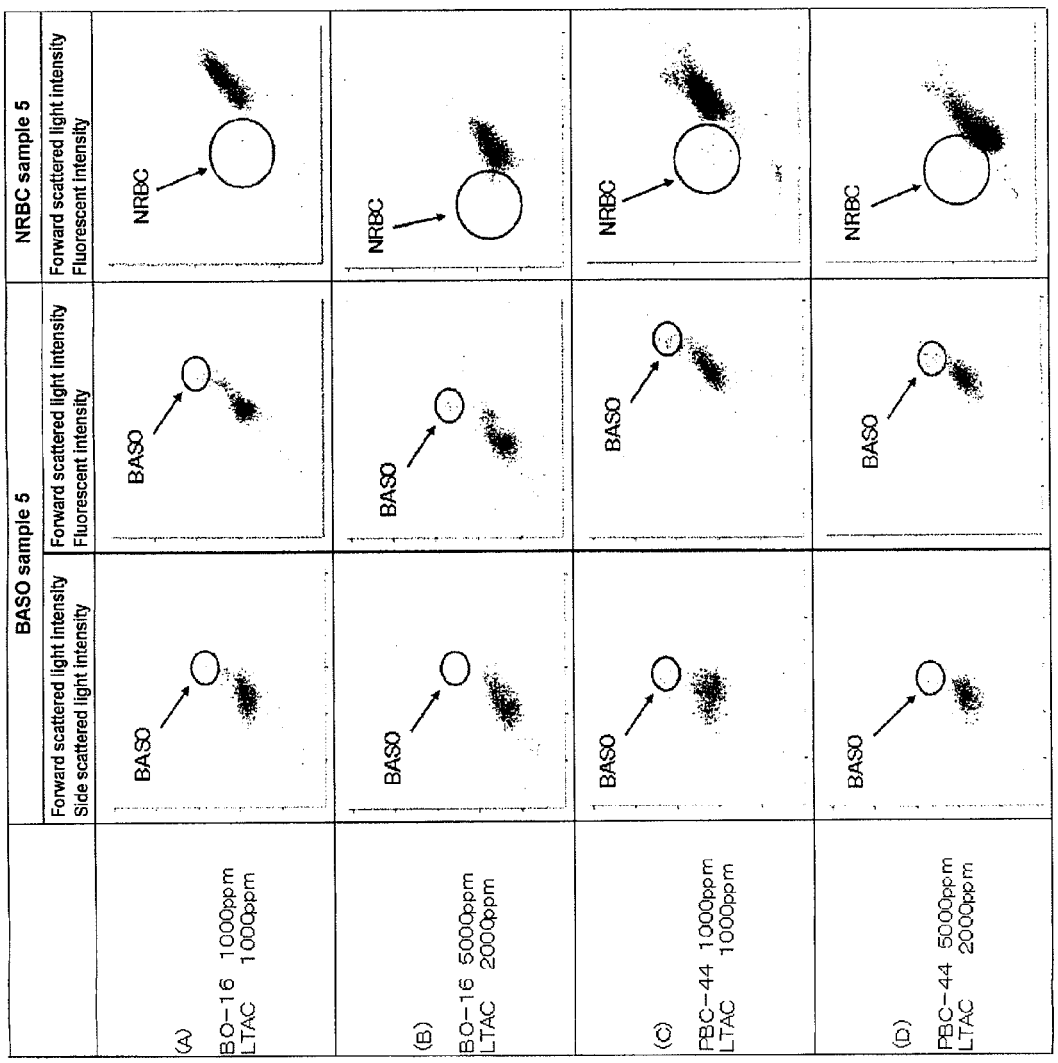
FIG. 11 represents scattergrams when samples are analyzed using the sample analysis reagents in Example 4.
Figure 12:
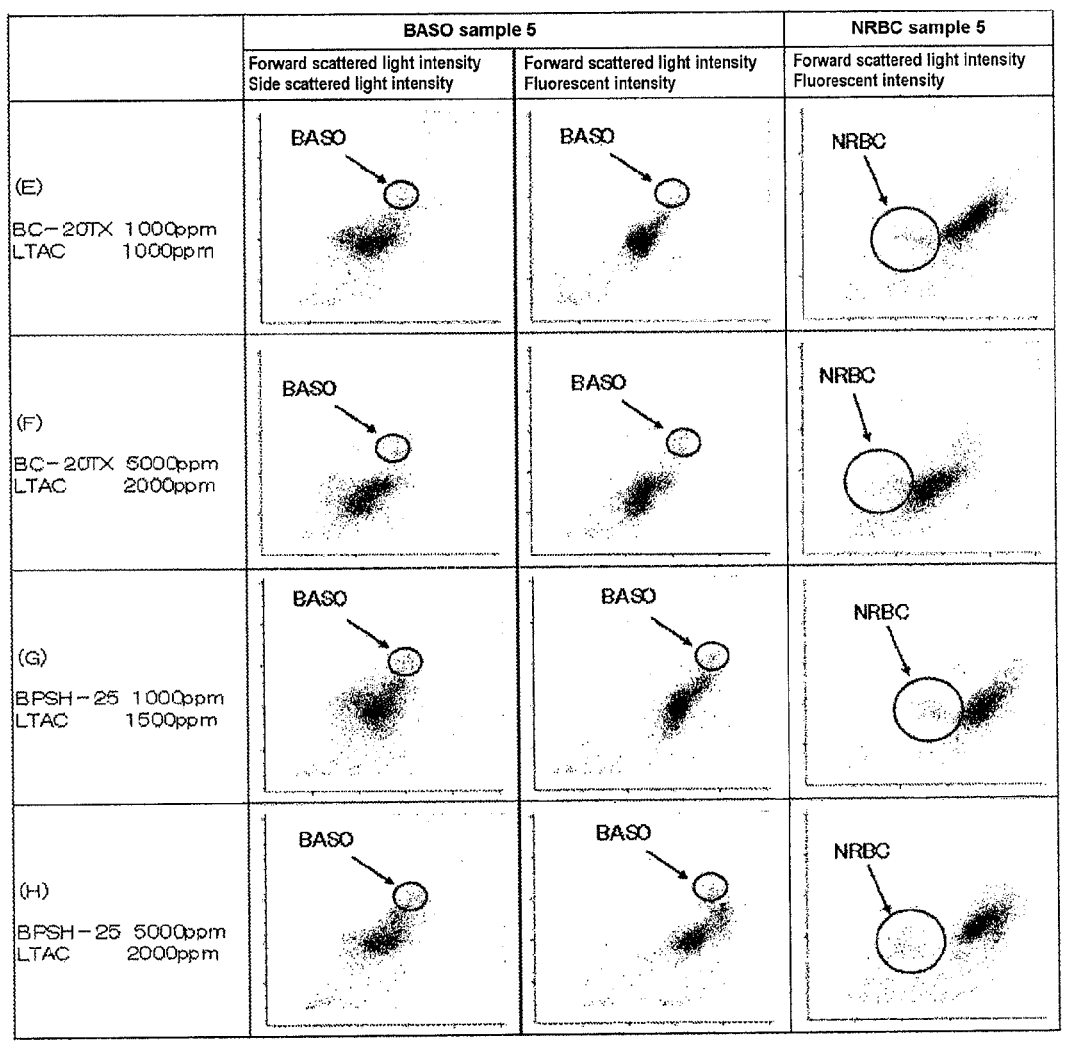
FIG. 12 represents scattergrams when samples are analyzed using the sample analysis reagents in Example 4.
Figure 13:
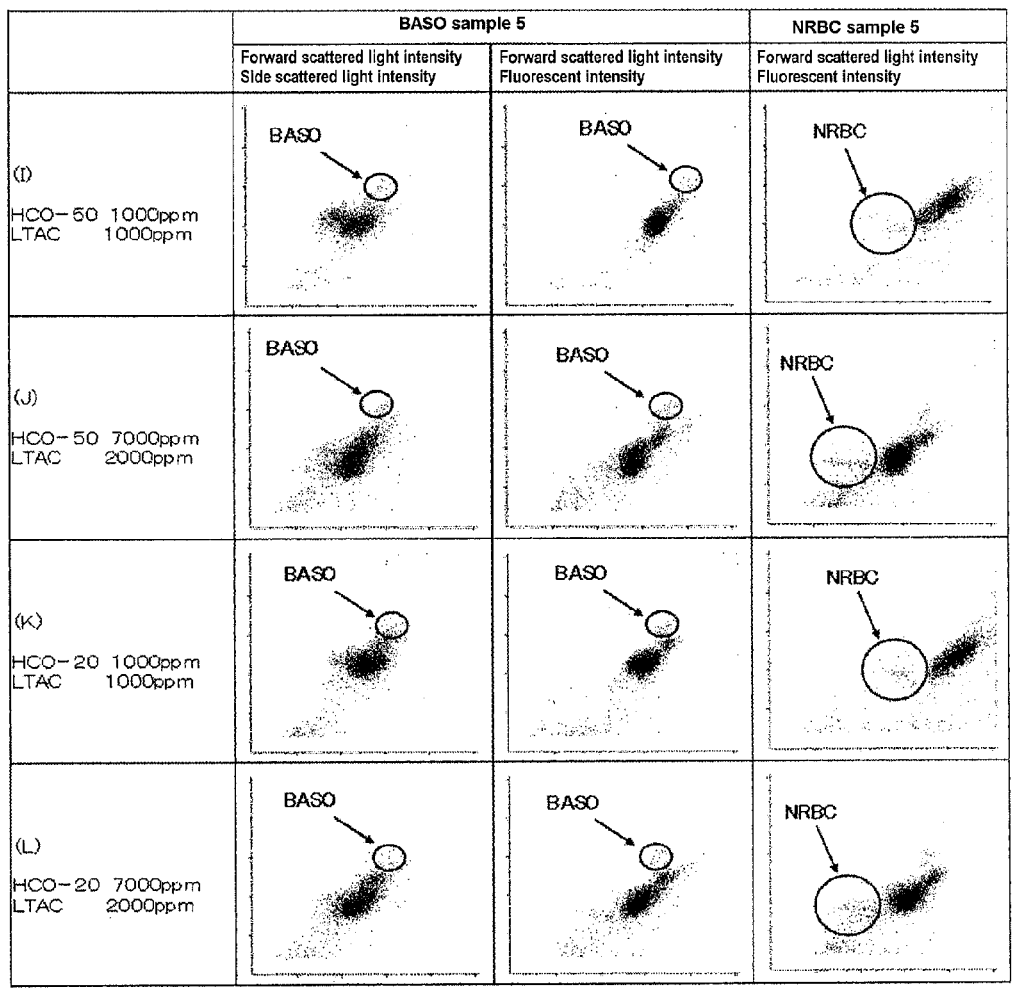
FIG. 13 represents scattergrams when samples are analyzed using the sample analysis reagents in Example 4.
Figure 14:
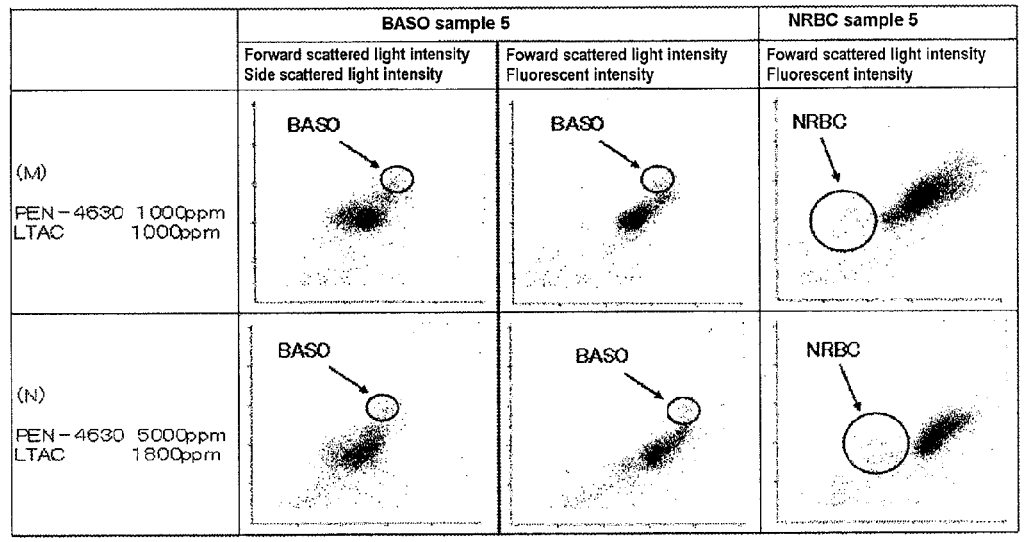
FIG. 14 represents scattergrams when samples are analyzed using the sample analysis reagents in Example 4.

Similar to Example 1, a first scattergram having two axes of the forward scattered light intensity and the fluorescent intensity and a second scattergram having two axes of the forward scattered light intensity and the side scattered light intensity were obtained for the measurement sample. FIG. 5 shows the first and second scattergrams obtained by the measurements on BASO samples 2 for which about 50 hours have passed after their collection, and the first scattergram obtained by the measurements on NRBC samples 2 for which about 50 hours have passed after their collection. FIG. 6 shows the first and second scattergrams obtained by the measurements on BASO samples 3 for which about 50 hours have passed after their collection, and the first scattergram obtained by the measurements on NRBC samples 3 for which about 50 hours have passed after their collection.

Based on these scattergrams, total leukocytes, basophils and nucleated erythrocytes were counted and the ratio of basophils and the ratio of nucleated erythrocytes were calculated. Table 4 shows the ratios of basophils of BASO sample 2 and 3 for which about 50 hours have passed after its collection, which were calculated in this Example. Table 4 represents the respective ratios of basophils calculated according to the first scattergram (the forward scattered light intensity and the fluorescent intensity) and the second scattergram (the forward scattered light intensity and the side scattered light intensity). Table 5 shows the ratios of nucleated erythrocytes of NRBC samples 2 and 3 for which about 50 hours have passed after its collection, which were calculated in this Example.

TABLE 4

| | | Ratio of basophils (%) | |
|---|---|---|---|
| Samples used | Reagents used | Forward scattered light intensity Side scattered light intensity | Forward scattered light intensity Fluorescent intensity |
| BASO sample 2 (50 hours after blood collection) | First reagent A and second reagent | 3.6 | 3.3 |
| | First reagent B and second reagent | 3.6 | 3.6 |
| | First reagent E and second reagent | 3.6 | 3.5 |
| | First reagent F and second reagent | 3.4 | 3.4 |
| BASO sample 3 (50 hours after | First reagent C and second reagent | 1.6 | 1.6 |

TABLE 4-continued

| | | Ratio of basophils (%) | |
|---|---|---|---|
| Samples used | Reagents used | Forward scattered light intensity Side scattered light intensity | Forward scattered light intensity Fluorescent intensity |
| blood collection) | First reagent D and second reagent | 1.8 | 1.9 |

TABLE 5

| Samples used | Reagents used | Ratio of nucleated erythrocytes (cells/100 WBCs) |
|---|---|---|
| NRBC sample 2 (50 hours after blood collection) | First reagent A and second reagent | 1.9 |
| | First reagent B and second reagent | 1.8 |
| | First reagent E and second reagent | 1.8 |
| | First reagent F and second reagent | 1.8 |
| NRBC sample 3 (50 hours after blood collection) | First reagent C and second reagent | 1.1 |
| | First reagent D and second reagent | 1.2 |

FIGS. 5 and 6 show that basophils in the samples for which about 50 hours have passed after their collection are clearly discriminated from leukocytes other than basophils when the sample analysis reagents according to this Example were used. Further, it is shown that nucleated erythrocytes in the samples for which about 50 hours have passed after their collection are clearly discriminated from basophils and leukocytes other than basophils when the sample analysis reagents according to the present embodiment were used. Thus, because basophils and nucleated erythrocytes are clearly discriminated respectively even in the samples for which a lapse of time has passed after their collection, the number and ratio thereof to total leukocytes were precisely obtained by identifying cells appearing in certain areas on the scattergrams as shown in FIGS. 5 and 6 as basophils and nucleated erythrocytes.

When the measurements were carried out by the method of Comparative Example 1, the ratios of basophils of BASO samples 2 and 3 for which about 8 hours have passed after their collection were 3.4% and 1.6%, respectively. The ratios of nucleated erythrocytes of NRBC samples 2 and 3 for which about 8 hours have passed after their collection were 1.9 and 1.3 cells/100 WBCs, respectively. Based on these results in Comparative Example 1 and in Tables 4 and 5, the ratios calculated in Example 2 were closely analogous to the ratios calculated in Comparative Example 1. Therefore, it was confirmed that nucleated erythrocytes and basophils can be measured, even in the blood samples for which a lapse of time have passed after their collection, with the sample analysis reagents of the present Example as precisely as the case when other reagent was used for the measurements.

Further, according to the results of BASO sample 2 in Tables 2 and 4, the ratio of basophils calculated for the sample for which about 50 hours have passed after its collection was closely analogous to the ratio of basophils calculated for the sample for which about 8 hours have passed after its collection. According to the results of NRBC sample 2 in Tables 3 and 5, the ratio of nucleated erythrocytes calculated for the sample for which about 50 hours have passed after its collection was closely analogous to the ratio of nucleated erythrocytes calculated for the sample for which about 8 hours have passed after its collection.

Accordingly, it was confirmed that highly precise measurements can be carried out with the sample analysis reagents of this Example, even when the sample for which a lapse of time has passed after its collection is used.

Example 3

In this Example, the combinations of the cationic surfactant, DTAB, and various nonionic surfactants were studied. The first and second reagents having the following compositions were prepared. The pH of the first reagent is 3.0.
First Reagent A:
It is the aqueous solution containing 10 mM of sodium salicylate, 3000 ppm of BO-16 and 3000 ppm of DTAB.
First Reagent B:
It is the aqueous solution containing 10 mM of sodium salicylate, 7000 ppm of BO-16 and 7000 ppm of DTAB.
First Reagent C:
It is the aqueous solution containing 10 mM of sodium salicylate, 3000 ppm of PBC-44 and 5000 ppm of DTAB.
First Reagent D:
It is the aqueous solution containing 10 mM of sodium salicylate, 7000 ppm of PBC-44 and 7000 ppm of DTAB.
First Reagent E:
It is the aqueous solution containing 10 mM of sodium salicylate, 2000 ppm of BC-20TX and 3000 ppm of DTAB.
First Reagent F:
It is the aqueous solution containing sodium salicylate 10 mM, 2000 ppm of BC-20TX and 5000 ppm of DTAB.
First Reagent G:
It is the aqueous solution containing 10 mM of sodium salicylate, 3000 ppm of BPSH-25 and 7000 ppm of DTAB.
First Reagent H:
It is the aqueous solution containing 10 mM of sodium salicylate, 7000 ppm of BPSH-25 and 7000 ppm of DTAB.
First Reagent I:
It is the aqueous solution containing 10 mM of sodium salicylate, 5000 ppm of HCO-50 and 5000 ppm of DTAB.
First Reagent J:
It is the aqueous solution containing 10 mM of sodium salicylate, 7000 ppm of HCO-50 and 7000 ppm of DTAB.
First Reagent K:
It is the aqueous solution containing 10 mM of sodium salicylate, 3000 ppm of HCO-20 and 5000 ppm of DTAB.
First Reagent L:
It is the aqueous solution containing 10 mM of sodium salicylate, 7000 ppm of HCO-20 and 7000 ppm of DTAB.
First Reagent M:
It is the aqueous solution containing 10 mM of sodium salicylate, 3000 ppm of CO-20TX and 5000 ppm of DTAB.
First Reagent N:
It is the aqueous solution containing sodium salicylate 10 mM, 7000 ppm of CO-20TX and 7000 ppm of DTAB.
First Reagent O:
It is the aqueous solution containing 10 mM of sodium salicylate, 3000 ppm of PEN-4630 and 5000 ppm of DTAB.
First Reagent P:
It is the aqueous solution containing 10 mM of sodium salicylate, 5000 ppm of PEN-4630 and 7000 ppm of DTAB.
Second Reagent:
It is ethylene glycol containing 300 ppm of NK-3383.

The first reagent (1 mL), 20 µL of the second reagent and 20 µl of the blood sample for which the presence of BASO or NRBC has been confirmed (BASO sample 4 or NRBC sample 4) were mixed thoroughly, and thus obtained mixture was allowed to react at 41° C. for 10 seconds to obtain the measurement sample. Similar to Example 1, basophils, nucleated erythrocytes and total leukocytes in the measurement sample were measured using the automatic blood cell counter XE-2100. The blood samples for which about 8 hours have passed after their collection were examined.

For the measurement sample prepared from BASO sample 4, a first scattergram having two axes of the forward scattered light intensity and the fluorescent intensity and a second scattergram having two axes of the forward scattered light intensity and the side scattered light intensity were obtained. For the measurement sample prepared from NRBC sample 4, a scattergram having two axes of the forward scattered light intensity and the fluorescent intensity was obtained. FIGS. 7 to 10 show the respective scattergrams.

FIGS. 7 to 10 show that basophils are clearly discriminated from leukocytes other than basophils when the sample analysis reagents are used in which DTAB and the nonionic surfactant are combined. In addition, it is shown that nucleated erythrocytes are clearly discriminated from basophils and leukocytes other than basophils when the sample analysis reagents are used in which DTAB and the nonionic surfactant are combined.

It was also shown that basophils contained in BASO sample 4 used in this Example were clearly discriminated from leukocytes other than basophils in either of the second and first scattergrams which have two axes of the forward scattered light intensity and the side scattered light intensity, and two axes of the forward scattered light intensity and the fluorescent intensity, respectively.

Thus, because basophils and nucleated erythrocytes are clearly discriminated respectively, the number and ratio thereof to total leukocytes can be precisely obtained by identifying cells appearing in certain areas on the scattergrams, as shown in FIGS. 7 to 10, as basophils and nucleated erythrocytes.

Example 4

In this Example, the combinations of the cationic surfactant, LTAC, and various nonionic surfactants were studied. The first and second reagents having the following compositions were prepared. The pH of the first reagent is 3.0.
First Reagent A:
It is the aqueous solution containing 10 mM of sodium salicylate, 1000 ppm of BO-16 and 1000 ppm of LTAC.
First Reagent B:
It is the aqueous solution containing 10 mM of sodium salicylate, 5000 ppm of BO-16 and 2000 ppm of LTAC.
First Reagent C:
It is the aqueous solution containing 10 mM of sodium salicylate, 1000 ppm of PBC-44 and 1000 ppm of LTAC.
First Reagent D:
It is the aqueous solution containing 10 mM of sodium salicylate, 5000 ppm of PBC-44 and 2000 ppm of LTAC.
First Reagent E:
It is the aqueous solution containing 10 mM of sodium salicylate, 1000 ppm of BC-20TX and 1000 ppm of LTAC.
First Reagent F:
It is the aqueous solution containing 10 mM of sodium salicylate, 5000 ppm of BC-20TX and 2000 ppm of LTAC.
First Reagent G:
It is the aqueous solution containing 10 mM of sodium salicylate, 1000 ppm of BPSH-25 and 1500 ppm of LTAC.

First Reagent H:
It is the aqueous solution containing 10 mM of sodium salicylate, 5000 ppm of BPSH-25 and 2000 ppm of LTAC.
First Reagent I:
It is the aqueous solution containing 10 mM of sodium salicylate, 1000 ppm of HCO-50 and 1000 ppm of LTAC.
First Reagent J:
It is the aqueous solution containing 10 mM of sodium salicylate, 7000 ppm of HCO-50 and 2000 ppm of LTAC.
First Reagent K:
It is the aqueous solution containing 10 mM of sodium salicylate, 1000 ppm of HCO-20 and 1000 ppm of LTAC.
First Reagent L:
It is the aqueous solution containing 10 mM of sodium salicylate, 7000 ppm of HCO-20 and 2000 ppm of LTAC.
First Reagent M:
It is the aqueous solution containing 10 mM of sodium salicylate, 1000 ppm of PEN-4630 and 1000 ppm of LTAC.
First Reagent N:
It is the aqueous solution containing 10 mM of sodium salicylate, 5000 ppm of PEN-4630 and LTAC 1800 ppm.
Second Reagent:
It is ethylene glycol containing 300 ppm of NK-3383.

The first reagent (1 mL), 20 μL of the second reagent and 20 μl of the blood sample for which the presence of BASO or NRBC has been confirmed (BASO sample 5 or NRBC sample 5) were mixed thoroughly, and thus obtained mixture was allowed to react at 41° C. for 10 seconds to obtain the measurement sample. Similar to Example 1, basophils, nucleated erythrocytes and total leukocytes in the measurement sample were measured using the automatic blood cell counter XE-2100. The blood samples for which about 8 hours have passed after their collection were measured.

For the measurement sample prepared from BASO sample 5, a first scattergram having two axes of the forward scattered light intensity and the fluorescent intensity and a second scattergram having two axes of the forward scattered light intensity and the side scattered light intensity were obtained. For the measurement sample prepared from NRBC sample 5, a scattergram having two axes of the forward scattered light intensity and the fluorescent intensity was obtained. FIGS. 11 to 14 show the respective scattergrams.

FIGS. 11 to 14 show that basophils are clearly discriminated from leukocytes other than basophils when the sample analysis reagents are used in which LTAC and the nonionic surfactant are combined. In addition, it is shown that nucleated erythrocytes are clearly discriminated from basophils and leukocytes other than basophils when the sample analysis reagents are used in which LTAC and the nonionic surfactant are combined.

It was also shown that basophils contained in BASO sample 5 used in this Example were clearly discriminated from leukocytes other than basophils in either of the second and first scattergrams which have two axes of the forward scattered light intensity and the side scattered light intensity, and two axes of the forward scattered light intensity and the fluorescent intensity, respectively.

Thus, because basophils and nucleated erythrocytes are clearly discriminated respectively, the number and ratio thereof to total leukocytes can be precisely obtained by identifying cells appearing in certain areas on the scattergrams, as shown in FIGS. 11 to 14, as basophils and nucleated erythrocytes.

Examples 3 and 4 show that nucleated erythrocytes and basophils in blood samples can clearly be discriminated from other leukocytes and counted by using the sample analysis reagents in which cationic surfactants and nonionic surfactants are combined.

Example 5

In this Example, the combinations of aromatic carboxylic acids and buffering agents were studied. The first and second reagents having the following compositions were prepared. The pH of the first reagent is 3.0.
First Reagent A:
It is the aqueous solution containing 10 mM of potassium hydrogen phthalate, 0 mM of DL-malic acid, 1000 ppm of BO-16, and 2000 ppm of LTAC.
First Reagent B:
It is the aqueous solution containing 5 mM of potassium hydrogen phthalate, 5 mM of DL-malic acid 5 mM, 1000 ppm of BO-16 and 2000 ppm of LTAC.
First Reagent C:
It is the aqueous solution containing 1 mM of potassium hydrogen phthalate, 9 mM of DL-malic acid, 1000 ppm of BO-16 and 2000 ppm of LTAC.
First Reagent D:
It is the aqueous solution containing 0.3 mM of potassium hydrogen phthalate, 9.7 mM of DL-malic acid, 1000 ppm of BO-16 and 2000 ppm of LTAC.
First Reagent E:
It is the aqueous solution containing 5 mM of sodium salicylate, 5 mM of DL-malic acid, 1000 ppm of PBC-44 and 1500 ppm of LTAC.
First Reagent F:
It is the aqueous solution containing 1 mM of sodium salicylate, 9 mM of DL-malic acid, 1000 ppm of PBC-44 and 1500 ppm of LTAC.
First Reagent G:
It is the aqueous solution containing 0.22 mM of sodium salicylate, 10 mM of DL-malic acid, 1000 ppm of PBC-44 and 1500 ppm of LTAC.
First Reagent H:
It is the aqueous solution containing 5 mM of sodium salicylate, 5 mM of DL-malic acid, 1000 ppm of BO-16 and 2000 ppm of LTAC.
First Reagent I:
It is the aqueous solution containing 1 mM of sodium salicylate, 9 mM of DL-malic acid, 1000 ppm of BO-16 and 2000 ppm of LTAC.
First Reagent J:
It is the aqueous solution containing 0.24 mM of sodium salicylate, 10 mM of DL-malic acid, 1000 ppm of BO-16 and 2000 ppm of LTAC.
Second Reagent:
It is ethylene glycol containing 300 ppm of NK-3383.

The first reagent (1 mL), 20 μL of the second reagent and 20 μl of the blood sample for which the presence of BASO or NRBC has been confirmed (BASO sample 6 or NRBC sample 6) were mixed thoroughly, and thus obtained mixture was allowed to react at 41° C. for 10 seconds to obtain the measurement sample. Similar to Example 1, basophils, nucleated erythrocytes and total leukocytes in the measurement sample were measured using the automatic blood cell counter XE-2100. The blood samples for which about 8 hours have passed after their collection were measured.

For the measurement sample prepared from BASO sample 6, a first scattergram having two axes of the forward scattered light intensity and the fluorescent intensity and a second scattergram having two axes of the forward scattered light intensity and the side scattered light intensity were obtained.

Figure 15:
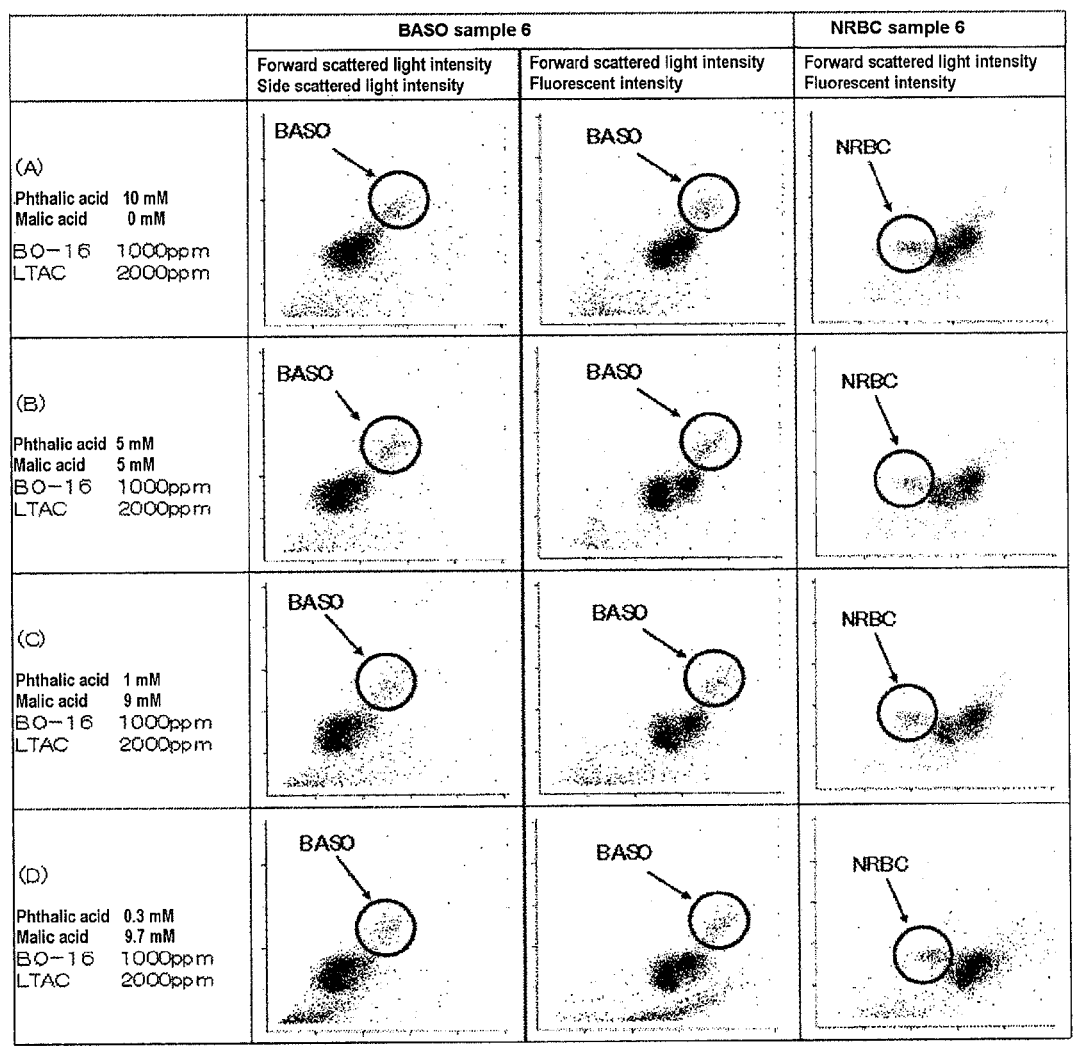
FIG. 15 represents scattergrams when samples are analyzed using the sample analysis reagents in Example 5.
Figure 16:
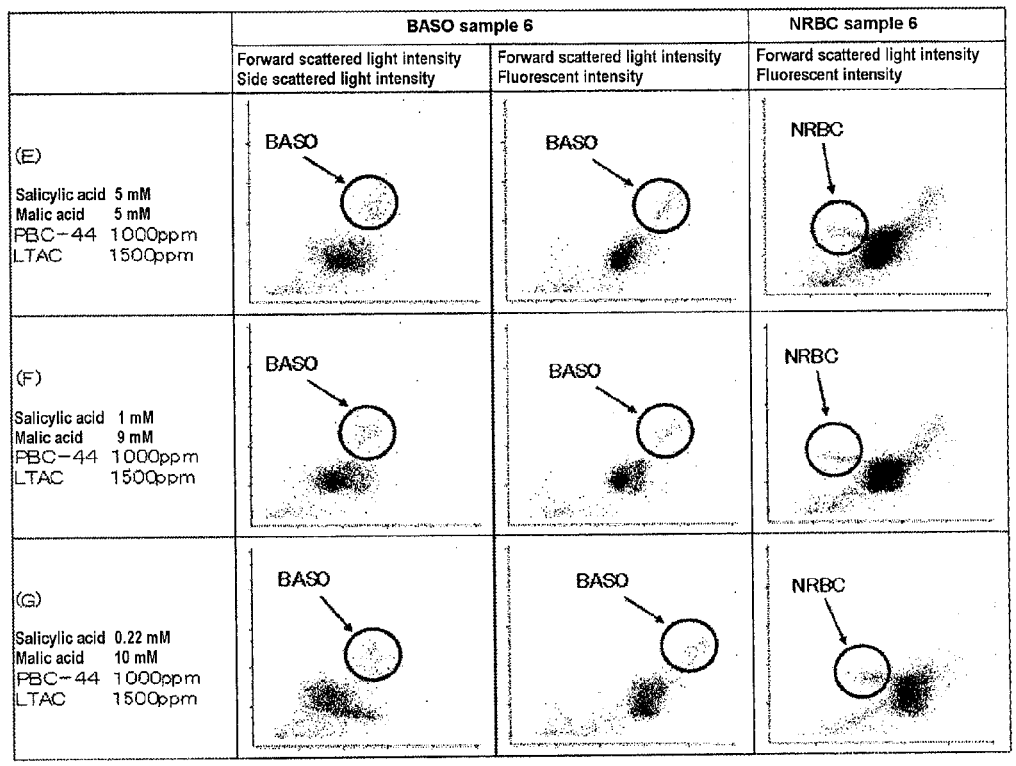
FIG. 16 represents scattergrams when samples are analyzed using the sample analysis reagents in Example 5.
Figure 17:
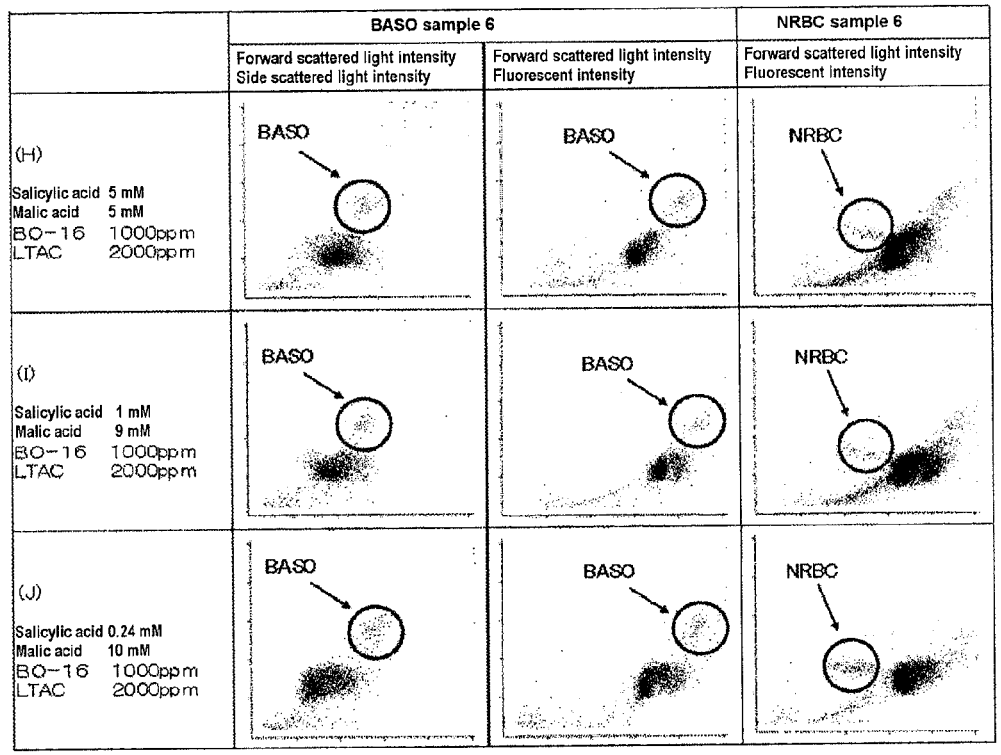
FIG. 17 represents scattergrams when samples are analyzed using the sample analysis reagents in Example 5.

For the measurement sample prepared from NRBC sample 6, a scattergram having two axes of the forward scattered light intensity and the fluorescent intensity was obtained. FIGS. 15 to 17 show the respective scattergrams.

FIGS. 15 to 17 show that basophils are clearly discriminated from leukocytes other than basophils when the sample analysis reagents are used in which the aromatic carboxylic acid and the buffering agent are combined. In addition, it is shown that nucleated erythrocytes are clearly discriminated from basophils and leukocytes other than basophils when the sample analysis reagents are used in which the aromatic carboxylic acid and the buffering agent are combined.

It was also shown that basophils contained in BASO sample 6 used in this Example were clearly discriminated from leukocytes other than basophils in either of the second and first scattergrams which have two axes of the forward scattered light intensity and the side scattered light intensity, and two axes of the forward scattered light intensity and the fluorescent intensity, respectively.

Thus, because basophils and nucleated erythrocytes are clearly discriminated respectively, the number and ratio thereof to total leukocytes can be precisely obtained by identifying cells appearing in certain areas on the scattergrams, as shown in FIGS. 15 to 17, as basophils and nucleated erythrocytes.

In FIG. 15, the barycenters of the clusters of nucleated erythrocytes, basophils and leukocytes other than basophils were identified, the values of the fluorescent intensity corresponding to the respective barycenters were obtained, and the obtained values were compared (data not shown). The barycenters of the respective clusters were obtained by a known method (see Japanese Unexamined Patent Publication HEI 5 (1993)-149863). As a result, it was shown that the difference between the fluorescent intensity of nucleated erythrocytes and the fluorescent intensity of basophils or leukocytes other than basophils is bigger when the sample analysis reagents containing both phthalic acid and malic acid (first reagents B to D) were used compared to the sample analysis reagents containing only phthalic acid (first reagent A). It was also shown that, among the sample analysis reagents containing both phthalic acid and malic acid (first reagents B to D), the difference between the fluorescent intensity of nucleated erythrocytes and the fluorescent intensity of basophils or leukocytes other than basophils is bigger for the reagent with higher concentration of malic acid (first reagents C and D).

Similar tendency was observed in FIGS. 16 and 17 for the sample analysis reagents containing salicylic acid and malic acid (first reagents E to J). As a result, it was shown that the discrimination performance of, particularly, nucleated erythrocytes is improved by combining the aromatic carboxylic acid and the buffering agent.

Example 6

In this Example, various fluorescent dyes were used as the fluorescent dye in the second reagent. The first and second reagents having the following compositions were prepared. The pH of the first reagent is 3.0.
First Reagent:
It is the aqueous solution containing 0.5 mM of potassium hydrogen phthalate, 10 mM of DL-malic acid, 1000 ppm of BO-16 and 2000 ppm of LTAC.
Second Reagent A:
It is ethylene glycol containing 150 ppm of NK-529.
Second Reagent B:
It is ethylene glycol containing 150 ppm of NK-2670.
Second Reagent C:
It is ethylene glycol containing 150 ppm of NK-3750.
Second Reagent D:
It is ethylene glycol containing 150 ppm of NK-3383.
Second Reagent E:
It is ethylene glycol containing 150 ppm of NK-1840.
Second Reagent F:
It is ethylene glycol containing 150 ppm of NK-9001.
Second Reagent G:
It is ethylene glycol containing 300 ppm of NK-9003.
Second Reagent H:
It is ethylene glycol containing 150 ppm of NK-2929.
Second Reagent I:
It is ethylene glycol containing 150 ppm of NK-3375.
Second Reagent J:
It is ethylene glycol containing 300 ppm of NK-5056.
Second Reagent K:
It is ethylene glycol containing 150 ppm of NK-3266.
Second Reagent L:
It is ethylene glycol containing 150 ppm of NK-3620.

The first reagent (1 mL), 20 µL of the second reagent and 20 µl of the blood sample for which the presence of BASO or NRBC has been confirmed (BASO sample 7 or NRBC sample 7) were mixed thoroughly, and thus obtained mixture was allowed to react at 41° C. for 10 seconds to obtain the measurement sample. Similar to Example 1, basophils, nucleated erythrocytes and total leukocytes in the measurement sample were measured using the automatic blood cell counter XE-2100.

The blood samples for which about 8 hours have passed after their collection were examined.

Figure 18:
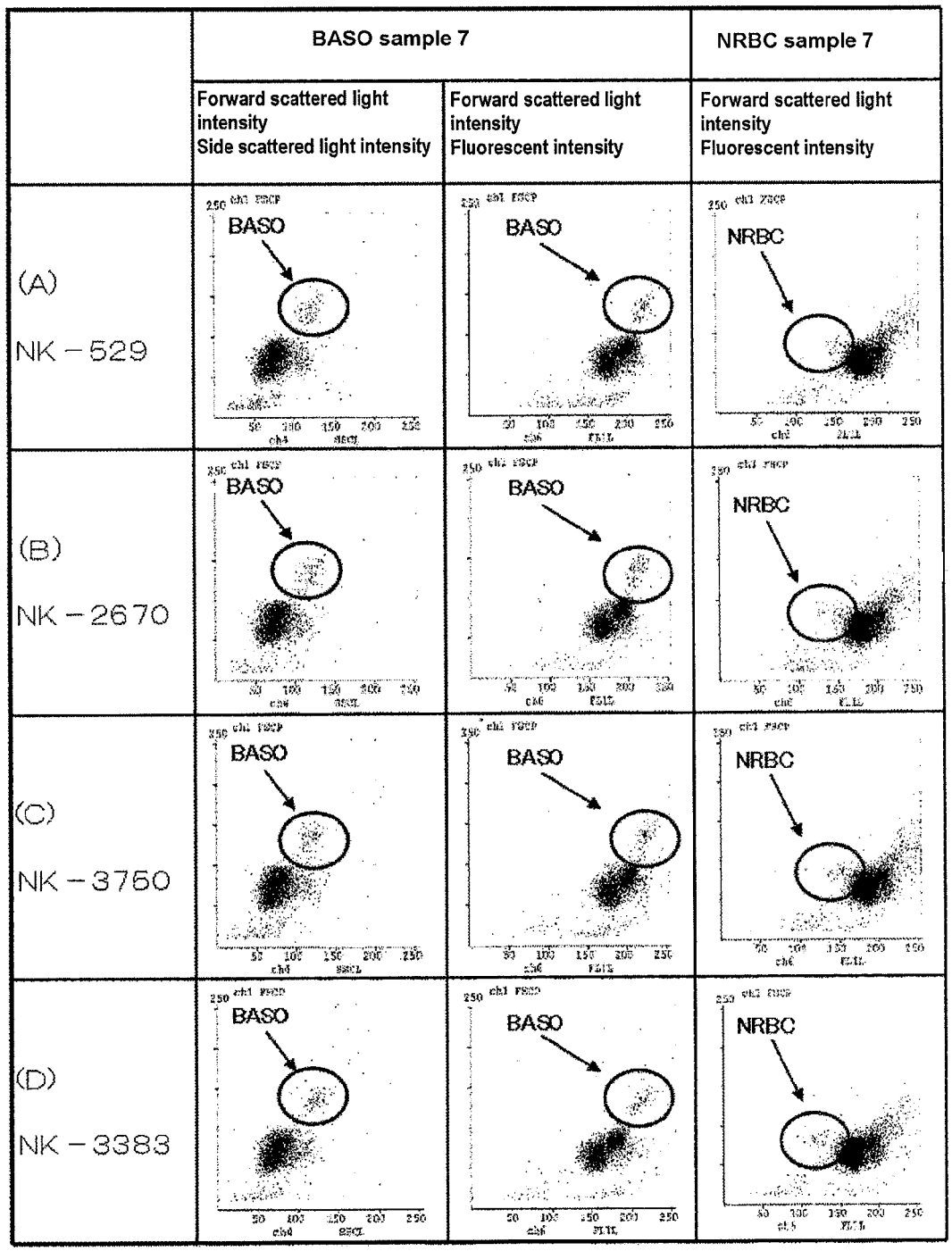
FIG. 18 represents scattergrams when samples are analyzed using the sample analysis reagents in Example 6.
Figure 19:
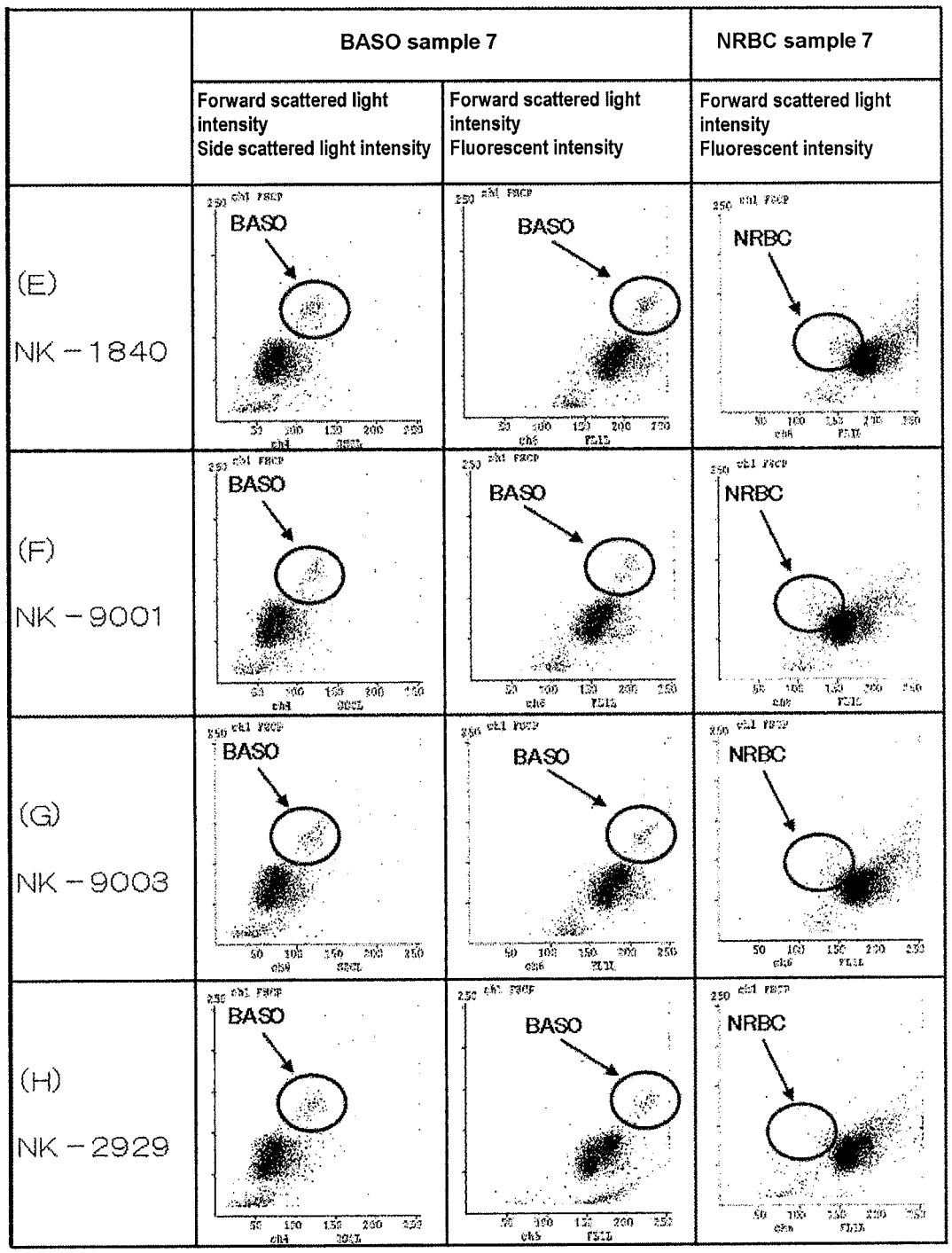
FIG. 19 represents scattergrams when samples are analyzed using the sample analysis reagents in Example 6.
Figure 20:
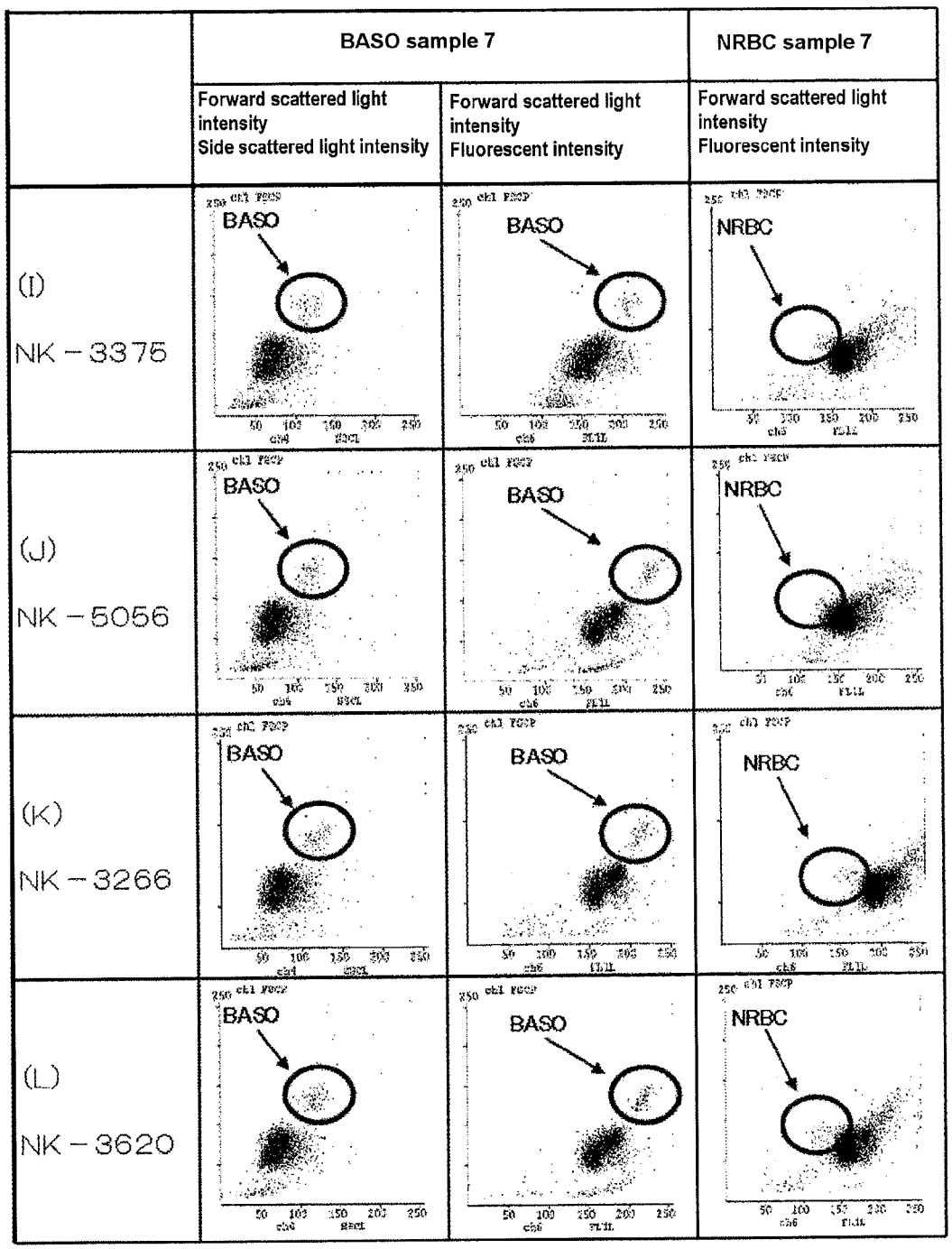
FIG. 20 represents scattergrams when samples are analyzed using the sample analysis reagents in Example 6.

For the measurement sample prepared from BASO sample 7, a first scattergram having two axes of the forward scattered light intensity and the fluorescent intensity and a second scattergram having two axes of the forward scattered light intensity and the side scattered light intensity were obtained. For the measurement sample prepared from NRBC sample 7, a scattergram having two axes of the forward scattered light intensity and the fluorescent intensity was obtained. FIGS. 18 to 20 show the respective scattergrams.

FIGS. 18 to 20 show that basophils are clearly discriminated from leukocytes other than basophils by using the sample analysis reagents containing any of the fluorescent dyes. In addition, it is shown that nucleated erythrocytes are clearly discriminated from basophils and leukocytes other than basophils by using the sample analysis reagents containing any of the fluorescent dyes.

It was also shown that basophils contained in BASO sample 7 used in this Example were clearly discriminated from leukocytes other than basophils in either of the second and first scattergrams which have two axes of the forward scattered light intensity and the side scattered light intensity, and two axes of the forward scattered light intensity and the fluorescent intensity, respectively.

Thus, because basophils and nucleated erythrocytes are clearly discriminated respectively, the number and ratio thereof to total leukocytes can be precisely obtained by identifying cells appearing in certain areas on the scattergrams, as shown in FIGS. 18 to 20, as basophils and nucleated erythrocytes.

Example 7

Study on the Type of Benzoic Acids

In this Example, potassium benzoate, sodium 4-hydroxybenzoate, sodium 3-hydroxybenzoate and potassium 4-aminobenzoate were used as aromatic carboxylic acids. The first and second reagents having the following compositions were prepared. The pH of the first reagent is 3.0.

First Reagent A:
It is the aqueous solution containing 2 mM of potassium benzoate, 8 mM of DL-malic acid, 1000 ppm of PBC-44 and 2500 ppm of LTAC.

First Reagent B:
It is the aqueous solution containing 3 mM of potassium benzoate, 7 mM of DL-malic acid, 1000 ppm of PBC-44 and 2500 ppm of LTAC.

First Reagent C:
It is the aqueous solution containing 4 mM of potassium benzoate, 6 mM of DL-malic acid, 1000 ppm of PBC-44 and 2500 ppm of LTAC.

First Reagent D:
It is the aqueous solution containing 7 mM of sodium 4-hydroxybenzoate, 3 mM of DL-malic acid, 1000 ppm of PBC-44 and 2500 ppm of LTAC.

First Reagent E:
It is the aqueous solution containing 8 mM of sodium 4-hydroxybenzoate, 2 mM of DL-malic acid, 1000 ppm of PBC-44 and 2500 ppm of LTAC.

First Reagent F:
It is the aqueous solution containing 4 mM of sodium 3-hydroxybenzoate, 6 mM of DL-malic acid, 1000 ppm of PBC-44 and 2500 ppm of LTAC.

First Reagent G:
It is the aqueous solution containing 5 mM of sodium 3-hydroxybenzoate, 5 mM of DL-malic acid, 1000 ppm of PBC-44 and 2500 ppm of LTAC.

First Reagent H:
It is the aqueous solution containing 1 mM of potassium benzoate, 9 mM of DL-malic acid, 2000 ppm of BO-16 and 2800 ppm of LTAC.

First Reagent I:
It is the aqueous solution containing 2 mM of potassium 4-aminobenzoate, 8 mM of DL-malic acid, 2000 ppm of BO-16 and 2800 ppm of LTAC.

The aqueous solution containing 2 mM of potassium hydrogen phthalate, 10 mM of DL-malic acid, 1000 ppm of PBC-44 and 2500 ppm of LTAC was used as a reference for the first reagents A to G, and the aqueous solution containing 0.5 mM of potassium hydrogen phthalate, 10 mM of DL-malic acid, 2000 ppm of BO-16 and 2800 ppm of LTAC was used as a reference for the first reagents H and I.

Second Reagent:
It is ethylene glycol containing 150 ppm of NK-3383.

The first reagent (1 mL), 20 μL of the second reagent and 20 μl of the blood sample for which the presence of BASO or NRBC has been confirmed (BASO samples 8 and 9 or NRBC samples 8 and 9) were mixed thoroughly, and thus obtained mixture was allowed to react at 41° C. for 7 seconds to obtain the measurement sample. Similar to Example 1, basophils, nucleated erythrocytes and total leukocytes in the measurement sample were measured using the automatic blood cell counter XE-2100. The blood samples for which about 8 hours have passed after their collection were examined.

Figure 21:
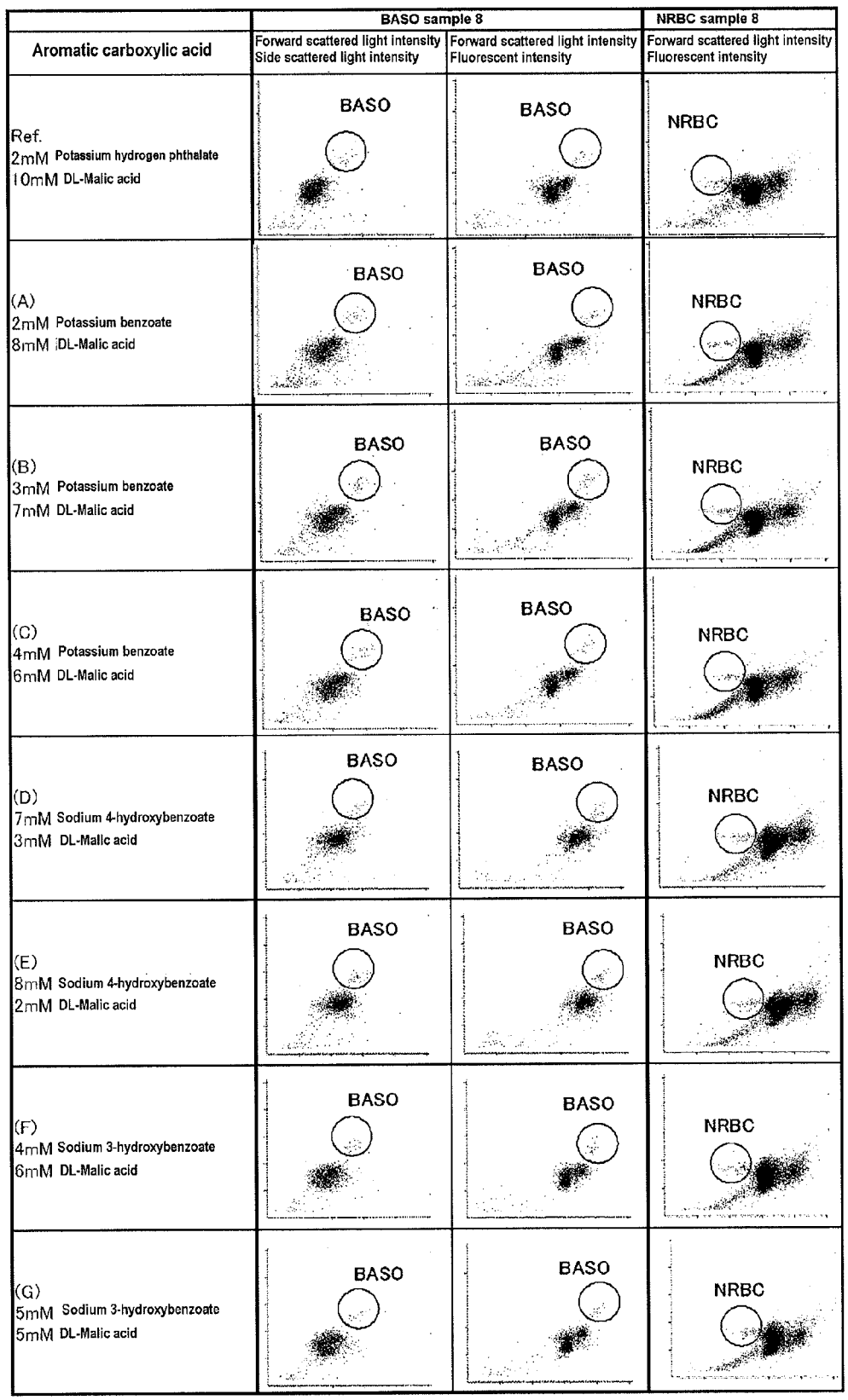
FIG. 21 represents scattergrams when samples are analyzed using the sample analysis reagents in Example 7.
Figure 22:
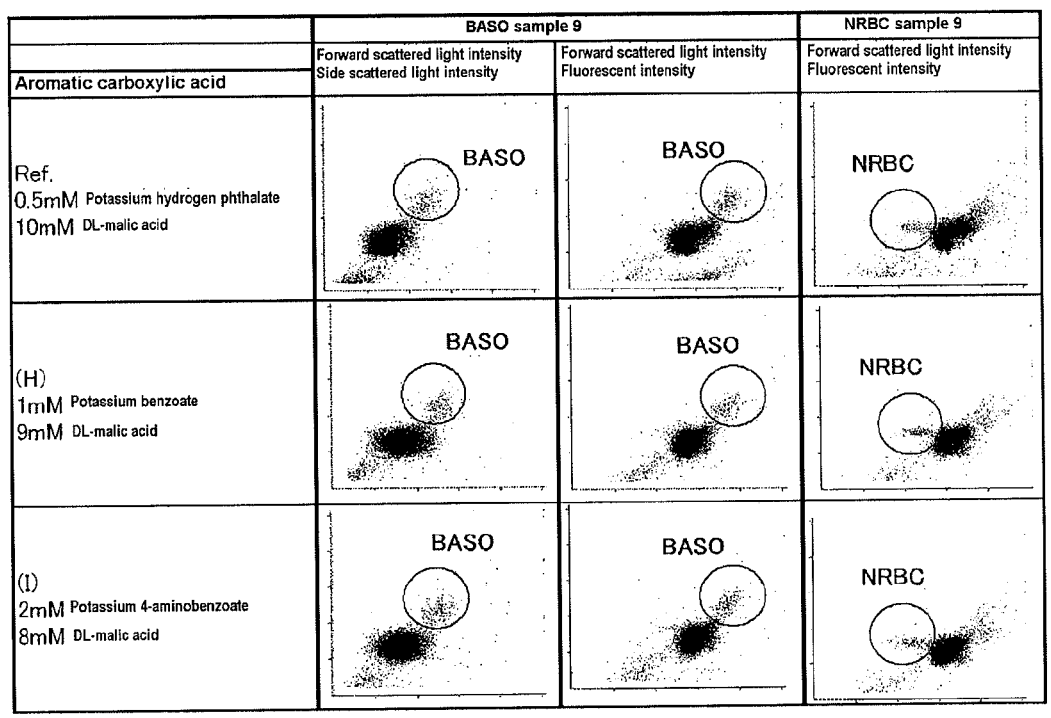
FIG. 22 represents scattergrams when samples are analyzed using the sample analysis reagents in Example 7.

For the measurement samples prepared from BASO samples 8 and 9, a first scattergram having two axes of the forward scattered light intensity and the fluorescent intensity and a second scattergram having two axes of the forward scattered light intensity and the side scattered light intensity were obtained. For the measurement samples prepared from NRBC samples 8 and 9, a scattergram having two axes of the forward scattered light intensity and the fluorescent intensity was obtained. FIGS. 21 and 22 show the respective scattergrams.

FIGS. 21 and 22 show that basophils are clearly discriminated from leukocytes other than basophils in any case. In addition, it is shown that nucleated erythrocytes are clearly discriminated from basophils and leukocytes other than basophils in any case.

It was also shown that basophils contained in BASO samples 8 and 9 used in this Example were clearly discriminated from leukocytes other than basophils in either of the second and first scattergrams which have two axes of the forward scattered light intensity and the side scattered light intensity, and two axes of the forward scattered light intensity and the fluorescent intensity, respectively.

Thus, because basophils and nucleated erythrocytes are clearly discriminated respectively, the number and ratio thereof to total leukocytes can be precisely obtained by identifying cells appearing in certain areas on the scattergrams, as shown in FIGS. 21 to 22, as basophils and nucleated erythrocytes.

Example 8

Combination of Potassium Hydrogen Phthalate and Potassium Benzoate

In this Example, the combinations of potassium hydrogen phthalate and potassium benzoate were studied as the aromatic carboxylic acids. The first and second reagents having the following compositions were prepared. The pH of the first reagent is 3.0.

First Reagent A:
It is the aqueous solution containing 2 mM of potassium hydrogen phthalate, 10 mM of DL-malic acid, 1000 ppm of PBC-44 and 2500 ppm of LTAC.

First Reagent B:
It is the aqueous solution containing 1.5 mM of potassium hydrogen phthalate, 0.5 mM of potassium benzoate, 10 mM of DL-malic acid, 1000 ppm of PBC-44 and 2500 ppm of LTAC.

First Reagent C:
It is the aqueous solution containing 1.33 mM of potassium hydrogen phthalate, 0.66 mM of potassium benzoate, 10 mM of DL-malic acid, 1000 ppm of PBC-44 and 2500 ppm of LTAC.

First Reagent D:
It is the aqueous solution containing 1 mM of potassium hydrogen phthalate, 1 mM of potassium benzoate, 10 mM of DL-malic acid, 1000 ppm of PBC-44 and 2500 ppm of LTAC.

First Reagent E:
It is the aqueous solution containing 0.66 mM of potassium hydrogen phthalate, 1.33 mM of potassium benzoate, 10 mM of DL-malic acid, 1000 ppm of PBC-44 and 2500 ppm of LTAC.

First Reagent F:
It is the aqueous solution containing 0.5 mM of potassium hydrogen phthalate, 1.5 mM of potassium benzoate, 10 mM of DL-malic acid, 1000 ppm of PBC-44 and 2500 ppm of LTAC.

First Reagent G:
It is the aqueous solution containing 2 mM of potassium benzoate, 10 mM of DL-malic acid, 1000 ppm of PBC-44 and 2500 ppm of LTAC.

Second Reagent:
It is ethylene glycol containing 150 ppm of NK-3383.

The first reagent (1 mL), 20 μL of the second reagent and 20 μl of the blood sample for which the presence of BASO or NRBC has been confirmed (BASO sample 10 or NRBC sample 10) were mixed thoroughly, and thus obtained mixture was allowed to react at 41° C. for 7 seconds to obtain the measurement sample. Similar to Example 1, basophils, nucleated erythrocytes and total leukocytes in the measurement sample were measured using the automatic blood cell counter XE-2100. The blood samples for which about 8 hours have passed after their collection were examined.

Figure 23:
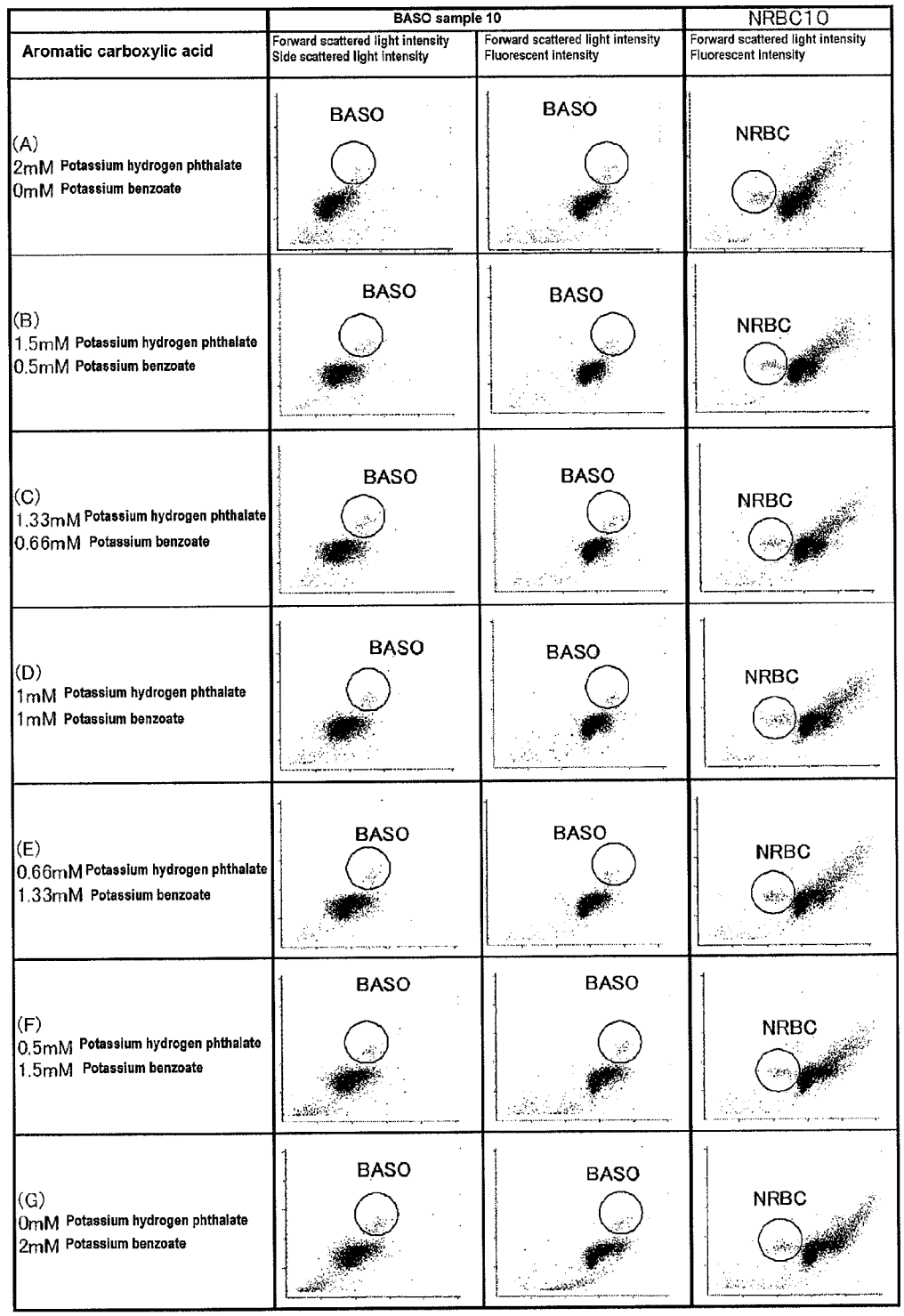
FIG. 23 represents scattergrams when samples are analyzed using the sample analysis reagents in Example 8.
Figure 24:
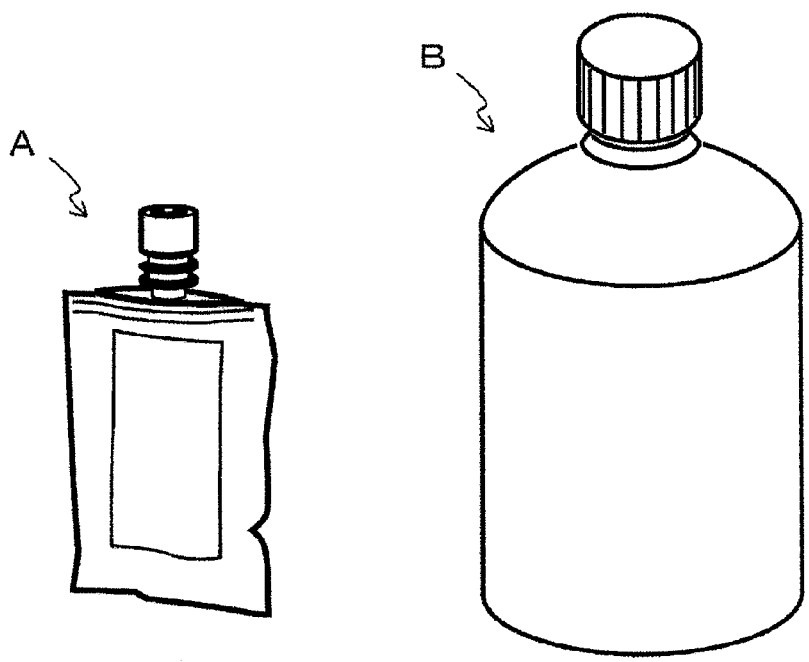
FIG. 24 shows a view of an exemplary reagent kit of the present invention. A: the second reagent; and B: the first reagent.

For the measurement sample prepared from BASO sample 10, a first scattergram having two axes of the forward scattered light intensity and the fluorescent intensity and a second scattergram having two axes of the forward scattered light intensity and the side scattered light intensity were obtained. For the measurement sample prepared from NRBC sample 10, a scattergram having two axes of the forward scattered light intensity and the fluorescent intensity was obtained. FIG. 23 shows the respective scattergrams.

FIG. 23 shows that basophils are clearly discriminated from leukocytes other than basophils in any case. In addition, it is shown that nucleated erythrocytes are clearly discriminated from basophils and leukocytes other than basophils in any case.

It was also shown that basophils contained in BASO sample 10 used in this Example were clearly discriminated from leukocytes other than basophils in either of the second and first scattergrams which have two axes of the forward scattered light intensity and the side scattered light intensity, and two axes of the forward scattered light intensity and the fluorescent intensity, respectively.

It is found that the amount of ghosts is advantageously reduced when potassium hydrogen phthalate is used and that WBC fraction and NRBC fraction are clearly discriminated with potassium benzoate. By using them in combination, basophils and nucleated erythrocytes are more clearly discriminated respectively.

Thus, because basophils and nucleated erythrocytes are clearly discriminated respectively, the number and ratio thereof to total leukocytes can be precisely obtained by identifying cells appearing in certain areas on the scattergrams, as shown in FIG. 23, as basophils and nucleated erythrocytes.

Example 9

Measurement of Blood Sample for which Little Time has Passed after its Collection In this Example, both NRBC and BASO were measured in blood samples for which little time has passed after their collection with the reagents of the present invention, by using a scattergram having the x-axis of the fluorescent intensity and the y-axis of the forward scattered light intensity. The first and second reagents having the following compositions were prepared.

First Reagent (Hemolysis Agent):
It is the aqueous solution containing 2 mM of potassium hydrogen phthalate, 10 mM of DL-malic acid, 1000 ppm of PBC-44 and 2000 ppm of LTAC. The pH of the first reagent is 3.0.

Second Reagent (Staining Solution):
It is ethylene glycol containing 50 ppm of NK-3383.
The blood samples used were:
Blood samples for which the presence of BASO has been confirmed (BASO samples): 12 samples; and
Blood samples for which the presence of NRBC has been confirmed (NRBC samples): 12 samples.

All blood samples are the ones for which about 2 to 7 hours have passed after their collection.

The first reagent (1 mL), 20 μL of the second reagent and 20 μl of the blood sample (BASO or NRBC sample) were mixed thoroughly, and thus obtained mixture was allowed to react at 41° C. for 7 seconds to obtain the measurement sample. Similar to Example 1, basophils, nucleated erythrocytes and total leukocytes in the measurement sample were measured using the automatic blood cell counter XE-2100.

Figure 25:
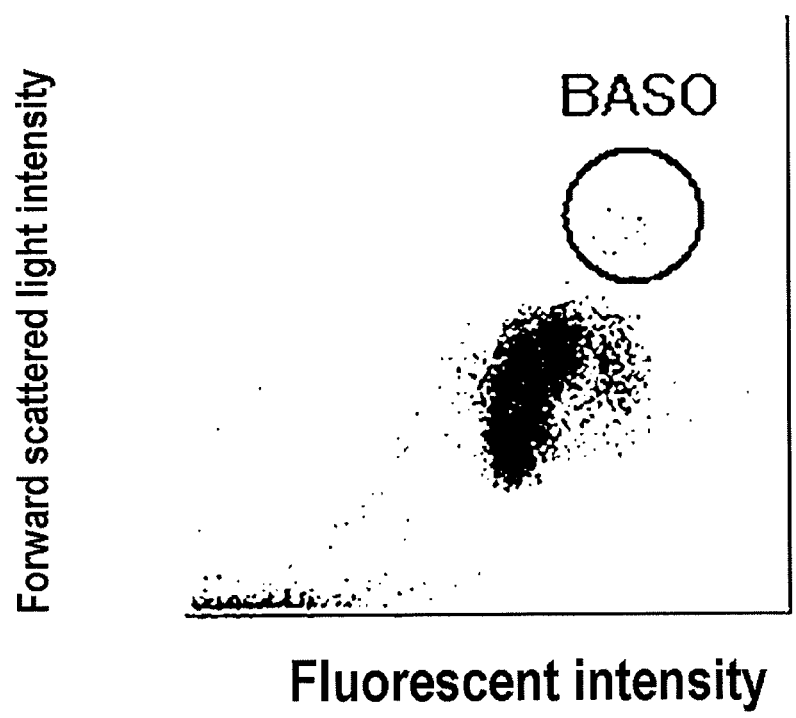
FIG. 25 represents scattergrams when samples are analyzed using the sample analysis reagents in Example 9.
Figure 26:
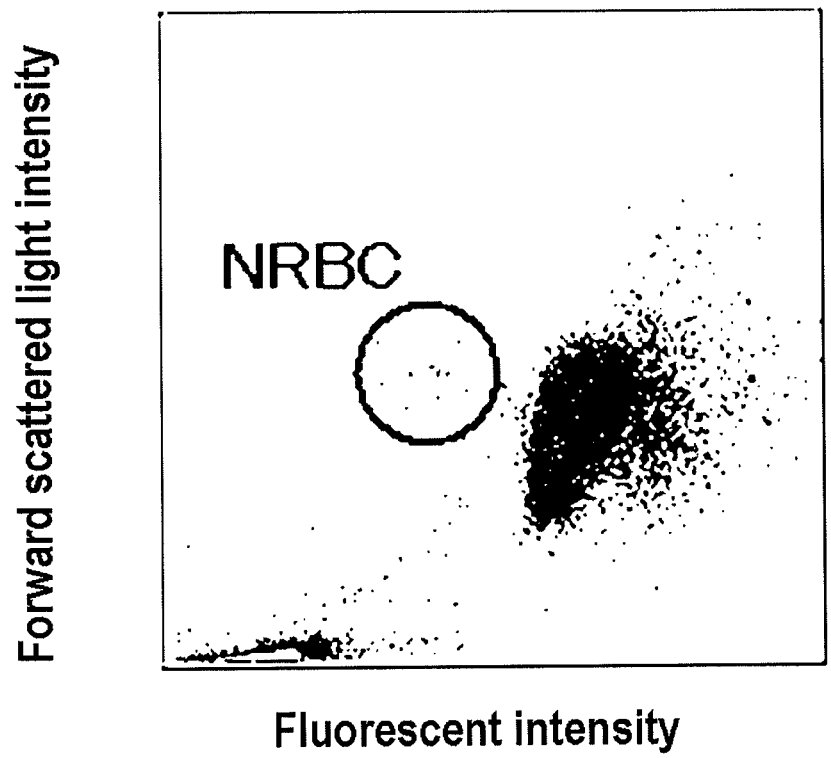
FIG. 26 represents scattergrams when samples are analyzed using the sample analysis reagents in Example 9.

For the measurement samples prepared from BASO or NRBC samples, scattergrams having two axes of the forward scattered light intensity and the fluorescent intensity were obtained. FIG. 25 shows one of the scattergrams from the measurement of BASO samples. FIG. 26 shows one of the scattergrams from the measurement of NRBC samples.

FIGS. 25 and 26 show that the present reagents allow the separation of NRBC and BASO in the blood samples for which little time has passed after their collection.

In the above scattergrams, total leukocytes, basophils and nucleated erythrocytes were identified as the cells appearing in certain regions and counted. The ratios of basophils and nucleated erythrocytes to total leukocytes were obtained from the obtained numbers of cells.

The numbers of total leukocytes, basophils and nucleated erythrocytes and the ratios of basophils and nucleated erythrocytes to total leukocytes were obtained as references for the same blood samples by the same procedure as Comparative Example 1.

Figure 27:
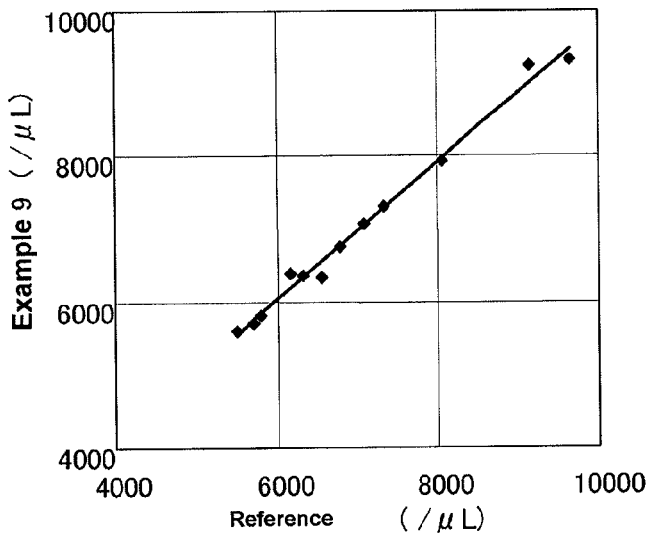
FIG. 27 shows graphs presenting correlations between the analysis results of a sample using the sample analysis reagents of Example 9 and the analysis results of the sample using a conventional method for sample analysis. (A) Correlation of the number of total leukocytes; (B) correlation of the ratio of basophils; and (C) correlation of the ratio of nucleated erythrocytes.
Figure 1:
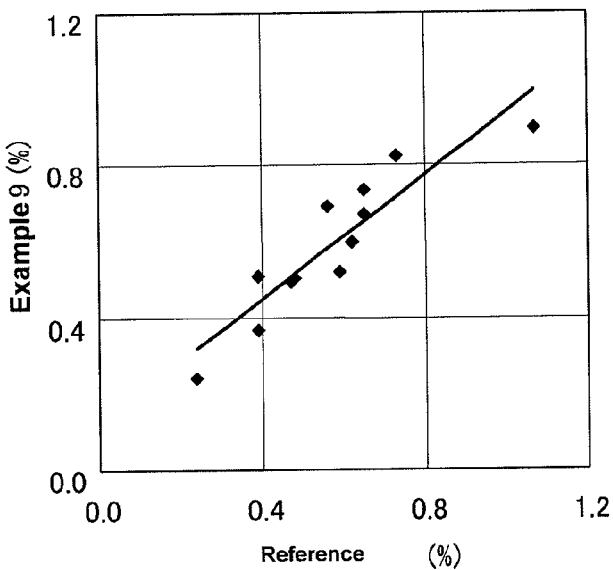
Figures 2, 27:
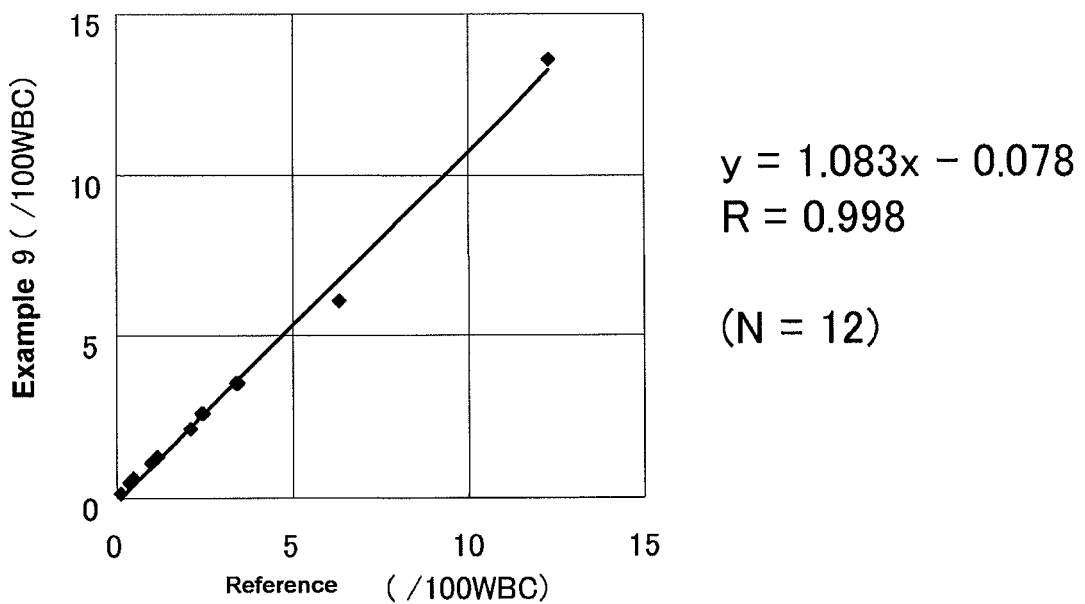

FIG. 27 shows correlations of the number of total leukocytes, the ratio of basophils and the ratio of nucleated erythrocytes between the results of the measurements with the above reagents (first reagent and second reagent) and those of the reference. The results of the number of total leukocytes for Example 9 and the reference shown in FIG. 27 were obtained from the measurement of BASO sample.

FIG. 27 shows that the correlation coefficients (r) between the results obtained with the present reagents and the reference in any of the number of total leukocytes, the ratio of basophils and the ratio of nucleated erythrocytes were 0.9 or more, showing strong correlation between them. Accordingly, it was found that NRBC and BASO can be measured with the present reagents in blood samples for which little time has passed after their collection.

The present application relates to Japanese Patent Application Nos. 2007-252666 and 2008-76606 respectively filed on Sep. 27, 2007 and Mar. 24, 2008, whose claims, specifications, drawings and abstracts are incorporated herein by reference.

The invention claimed is:
1. A reagent kit for analyzing a sample to measure basophils and/or nucleated erythrocytes in the sample comprising:
a first reagent containing a cationic surfactant, a nonionic surfactant and an aromatic carboxylic acid, which can lyse erythrocytes and damage a cell membrane of leukocytes so that a fluorescent dye can permeate therethrough, and
a second reagent containing the fluorescent dye capable of staining nucleic acid
wherein
said cationic surfactant is at least one selected from the group consisting of a quaternary ammonium salt and a pyridinium salt,
said nonionic surfactant is at least one selected from the group consisting of a polyoxyethylene alkyl ether, a polyoxyethylene polyoxypropylene alkyl ether, a polyoxyethylene castor oil, a polyoxyethylene hydrogenated castor oil, a polyoxyethylene sterol and a polyoxyethylene hydrogenated sterol, and
said fluorescent dye is at least one dye selected from the group consisting of a fluorescent dye having the general formula (I):

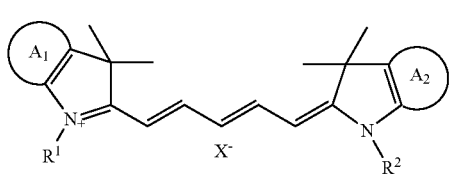

wherein:
$R^1$ and $R^2$ are, the same or different from each other, an alkyl group having 1 to 6 carbon atoms;

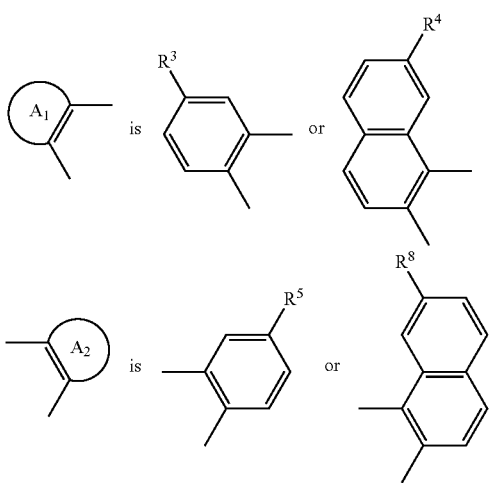

$R^3$, $R^4$, $R^5$, and $R^6$ are, the same or different from each other, a hydrogen atom or an alkyl group; and $X^-$ is an anion; and
a fluorescent dye having the general formula (II):

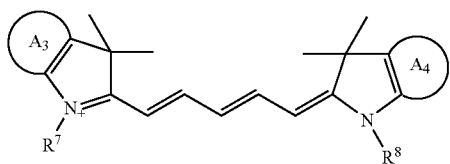

wherein:
$R^7$ and $R^8$ are, the same or different from each other, an alkyl group having 1 to 6 carbon atoms optionally containing an acidic group;

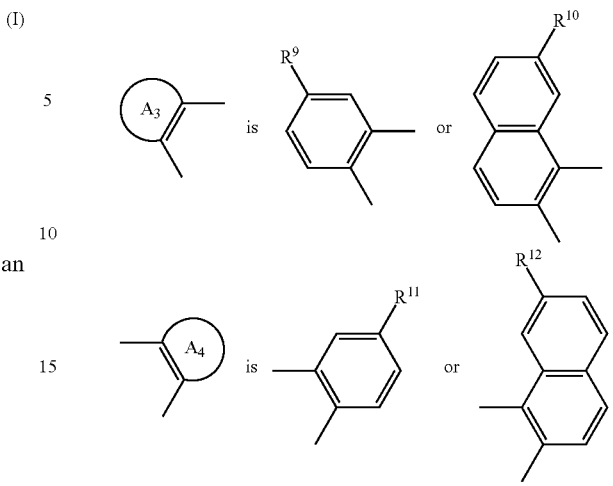

and $R^9$, $R^{10}$, $R^{11}$, and $R^{12}$ are, the same or different from each other, a hydrogen atom or an acidic group, provided that either one of $R^7$ to $R^{12}$ is/has an acidic group; and the acidic group which may be present in $R^7$ to $R^{12}$ may form a salt, provided that either one of the acidic group(s) which may be present in $R^7$ to $R^{12}$ is a group from which a proton has been liberated.

2. The reagent kit according to claim 1, wherein the acidic group which may present in $R^7$ to $R^{12}$ in the general formula (II) is a sulfonic group.

3. The reagent kit according to claim 1, wherein the acidic group forming the salt which may present in $R^7$ to $R^{12}$ in the general formula (II) is a group of an alkali metal salt.

4. The reagent kit according to claim 1, wherein the aromatic carboxylic acid is at least one selected from the group consisting of salicylic acid, phthalic acid, benzoic acid, hydroxybenzoic acid, aminobenzoic acid and a salt thereof.

5. The reagent kit according to claim 1, wherein pH of the first reagent is in acidic.

6. The reagent kit according to claim 1, wherein the first reagent comprises a buffering agent having pKa in the range of pH 2.0 to 4.5.

7. The reagent kit according to claim 6, wherein the buffering agent is at least one selected from the group consisting of malic acid, citric acid, tartaric acid, diglycolic acid, malonic acid and succinic acid.

8. The reagent kit according to claim 2, wherein the acidic group forming the salt which may be present in $R^7$ to $R^{12}$ in the general formula (II) is a group of an alkali metal salt.

* * * * *